United States Patent
Bradner et al.

(10) Patent No.: US 10,525,139 B2
(45) Date of Patent: Jan. 7, 2020

(54) FOLATE-CONJUGATED MOLECULES FOR DELIVERY OF TOXIC SMALL MOLECULE INHIBITORS TO CANCER CELLS AND METHODS OF USE

(71) Applicant: Dana-Farber Cancer Institute, Inc., Boston, MA (US)

(72) Inventors: James Bradner, Cambridge, MA (US); Kimberly Stegmaier, Jamaica Plain, MA (US); Jun Qi, Sharon, MA (US); Anthony Varca, Boston, MA (US); Giovanni Roti, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/523,518

(22) PCT Filed: Nov. 5, 2015

(86) PCT No.: PCT/US2015/059222
§ 371 (c)(1),
(2) Date: May 1, 2017

(87) PCT Pub. No.: WO2016/073708
PCT Pub. Date: May 12, 2016

(65) Prior Publication Data
US 2018/0280522 A1    Oct. 4, 2018

Related U.S. Application Data

(60) Provisional application No. 62/075,615, filed on Nov. 5, 2014.

(51) Int. Cl.
*A61K 31/365* (2006.01)
*A61K 47/55* (2017.01)
*C07D 475/04* (2006.01)
*C07D 307/93* (2006.01)
*A61K 31/519* (2006.01)

(52) U.S. Cl.
CPC .......... *A61K 47/551* (2017.08); *A61K 31/365* (2013.01); *A61K 31/519* (2013.01); *C07D 307/93* (2013.01); *C07D 475/04* (2013.01)

(58) Field of Classification Search
None
See application file for complete search history.

(56) References Cited

U.S. PATENT DOCUMENTS 5,475,092 A    12/1995   Chari et al.
6,368,598 B1    4/2002   D'Amico et al.

OTHER PUBLICATIONS

International Search Report and Written Opinion for International Application No. PCT/US15/59222 dated May 16, 2016.
Low et al., "Discovery and development of folic-acid-based receptor targeting for imaging and therapy of cancer and inflammatory diseases," Acc Chem Res, 41(1): 120-129 (2008).
Sapra et al., "Improved therapeutic responses in a xenograft model of human B lymphoma (Namalwa) for liposomal vincristine versus liposomal doxorubicin targeted via anti-CD19 IgG2a or Fab' fragments," Clin Cancer Res, 10(3): 1100-1111 (2004).

*Primary Examiner* — Samantha L Shterengarts
(74) *Attorney, Agent, or Firm* — Foley Hoag LLP

(57) ABSTRACT

The invention relates to novel derivatives of thapsigargin that are chemically modified with a group that targets a cell surface-expressed receptor, and pharmaceutical preparations thereof. The invention further relates to methods of treating diseases such as cancer using the compounds of the invention.

17 Claims, 21 Drawing Sheets

Folic acid-conjugated

Cancer

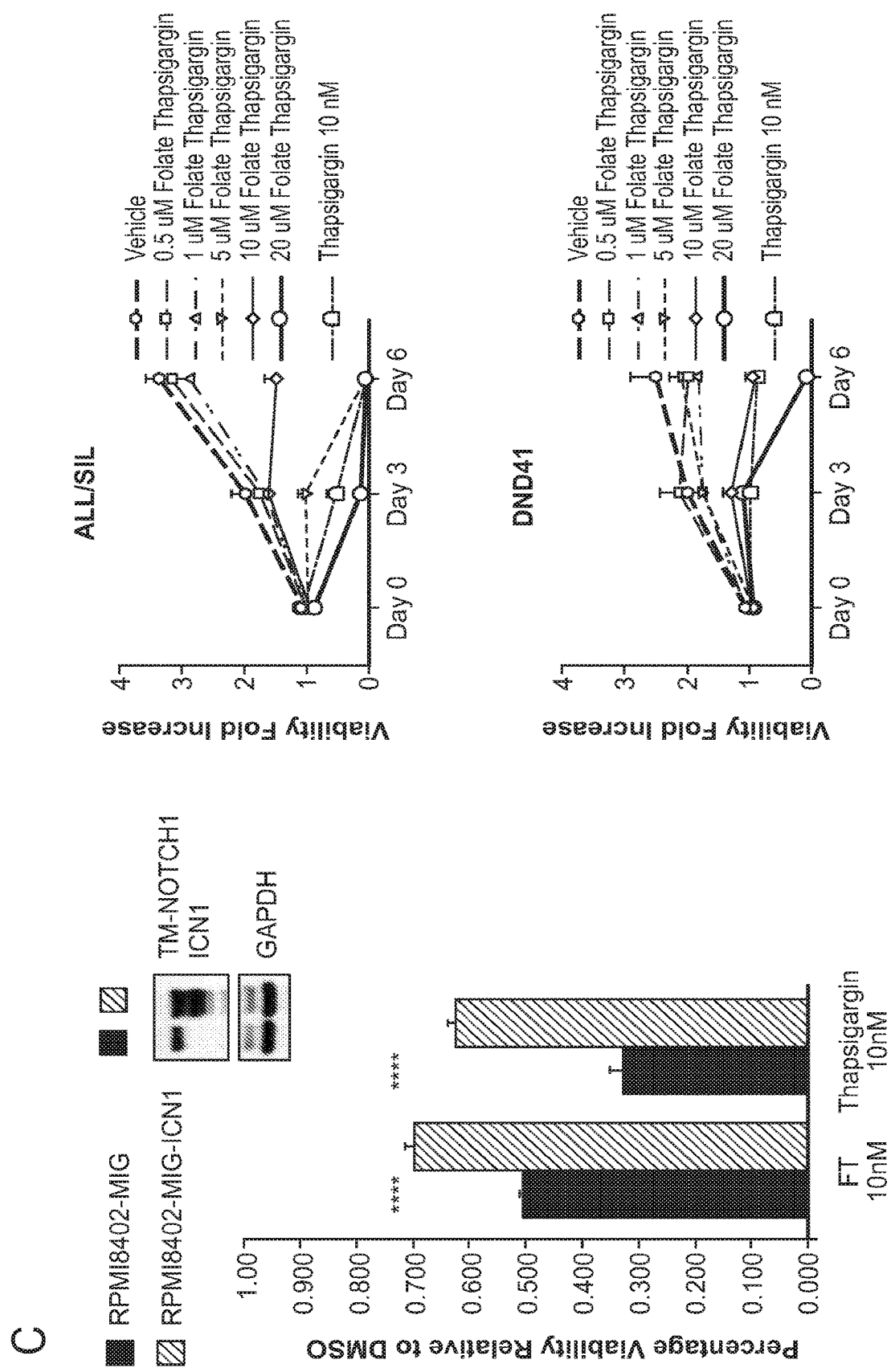
FIG. 2, continued

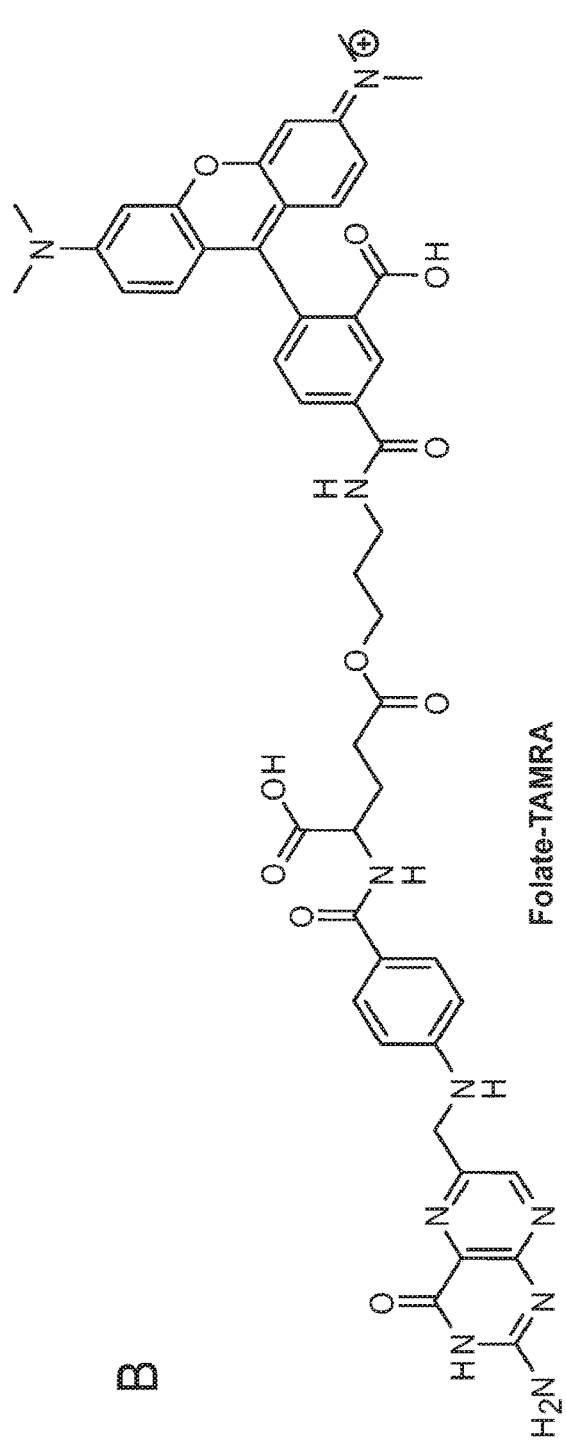
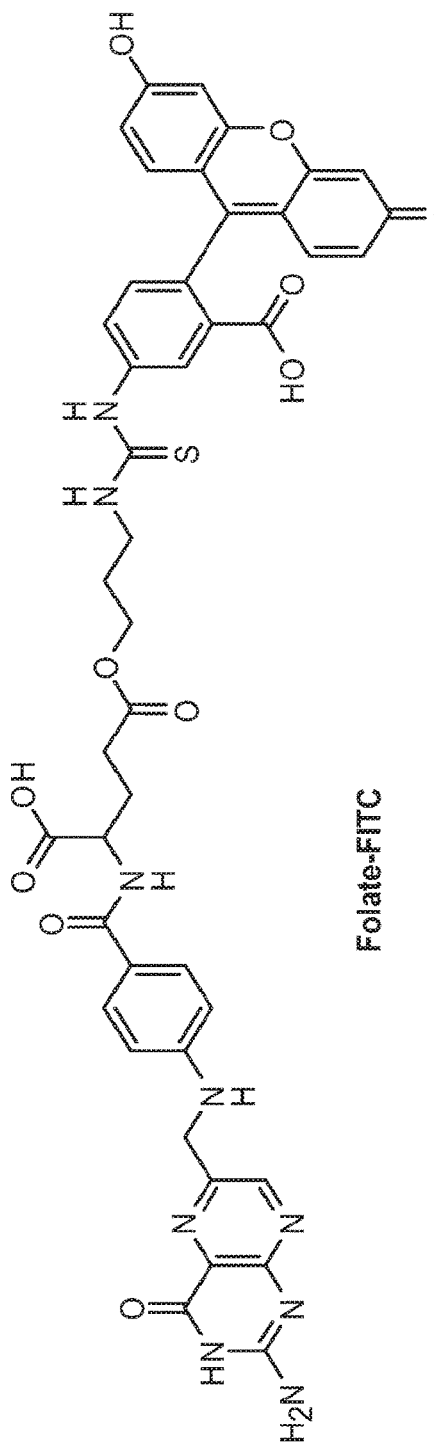
FIG. 3, continued

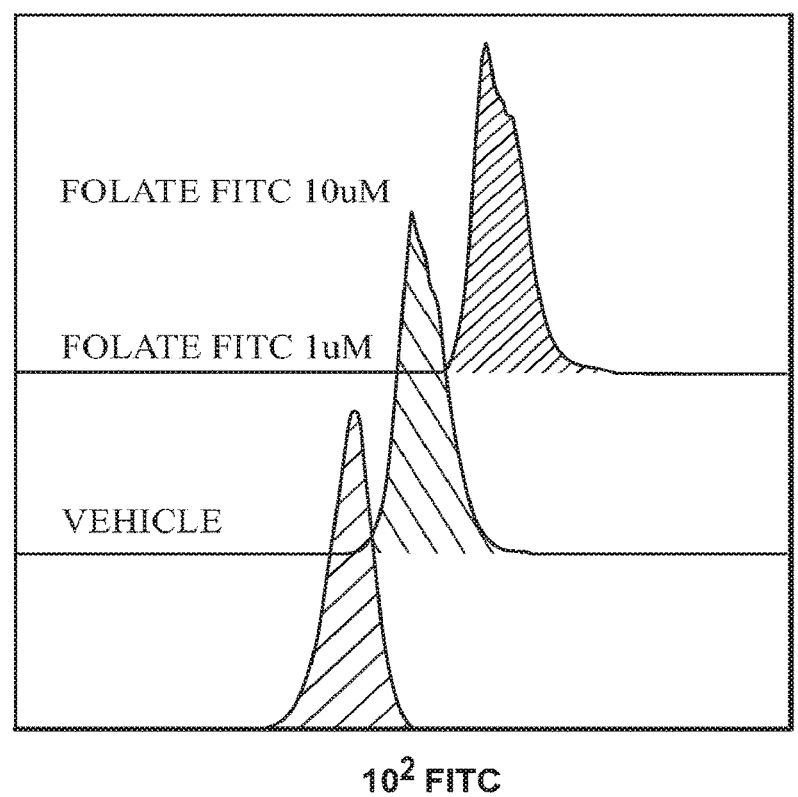
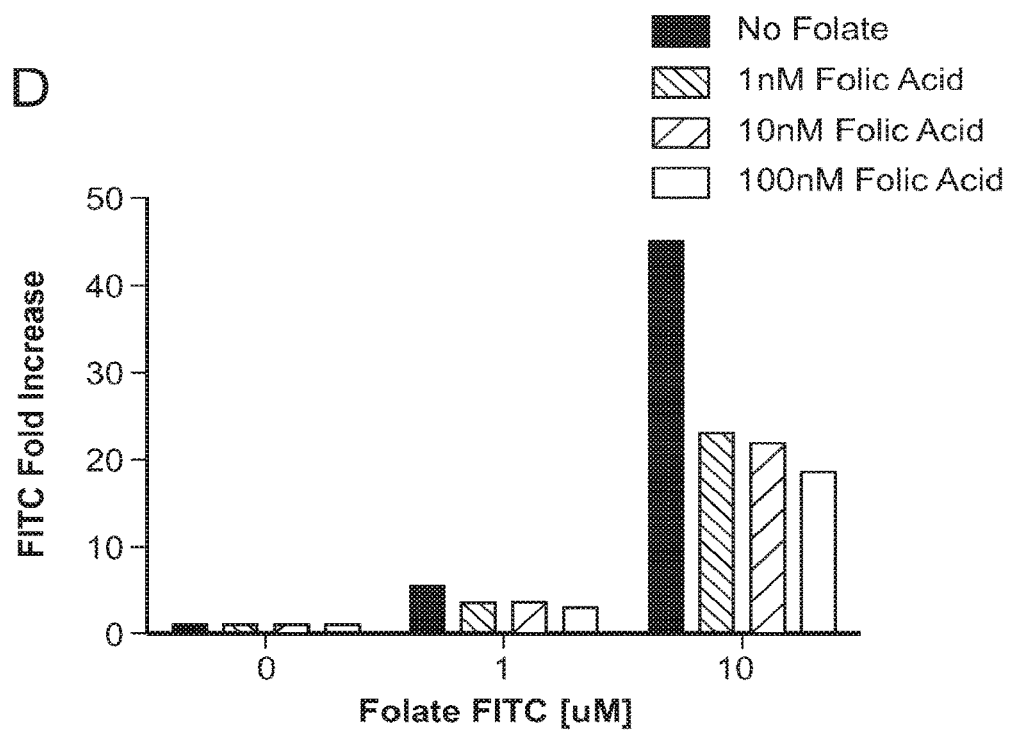
FIG. 3, continued

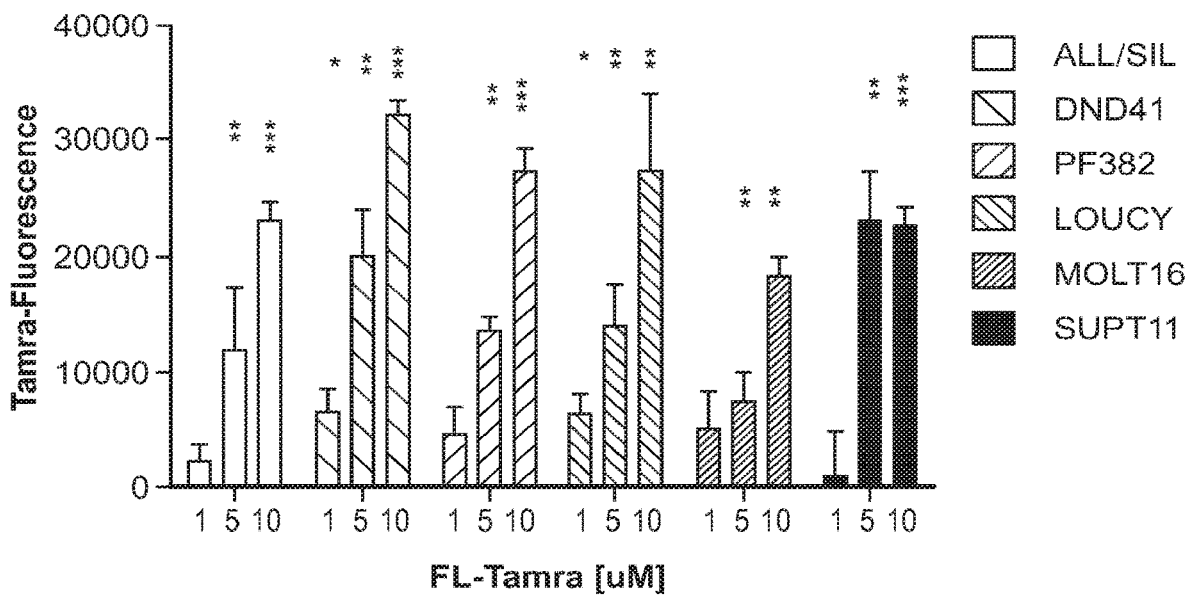
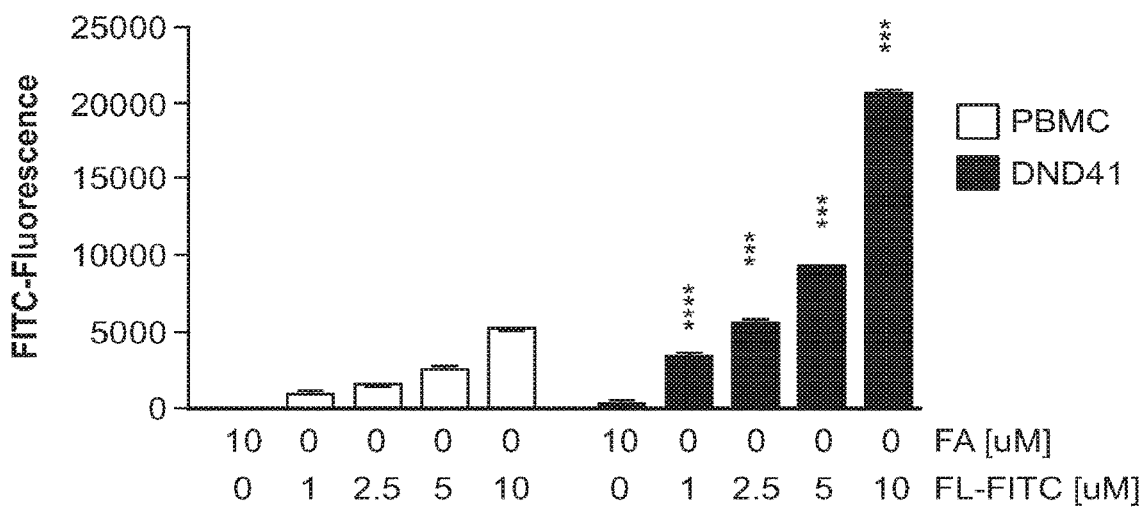
FIG. 7, continued

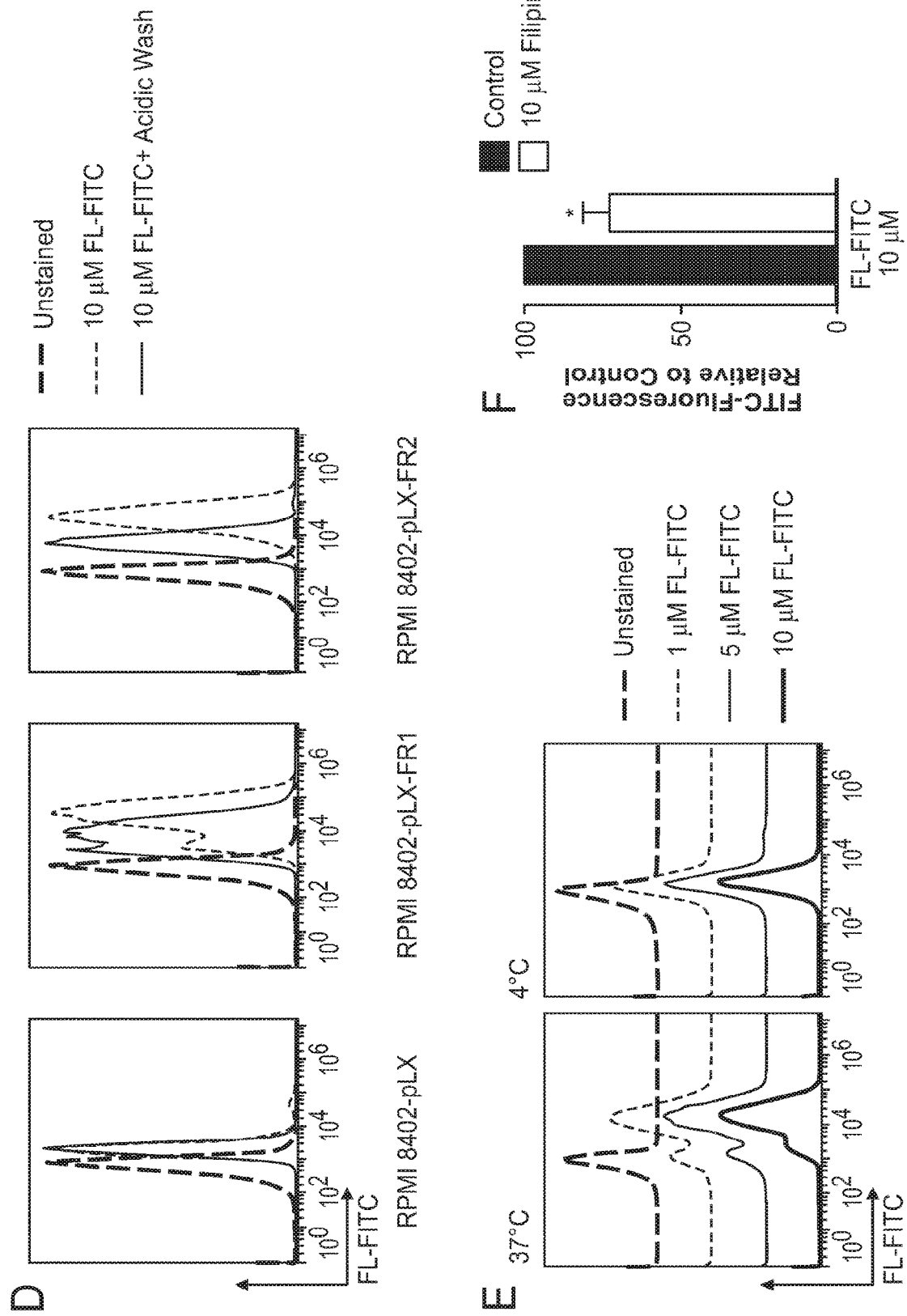
FIG. 8, continued

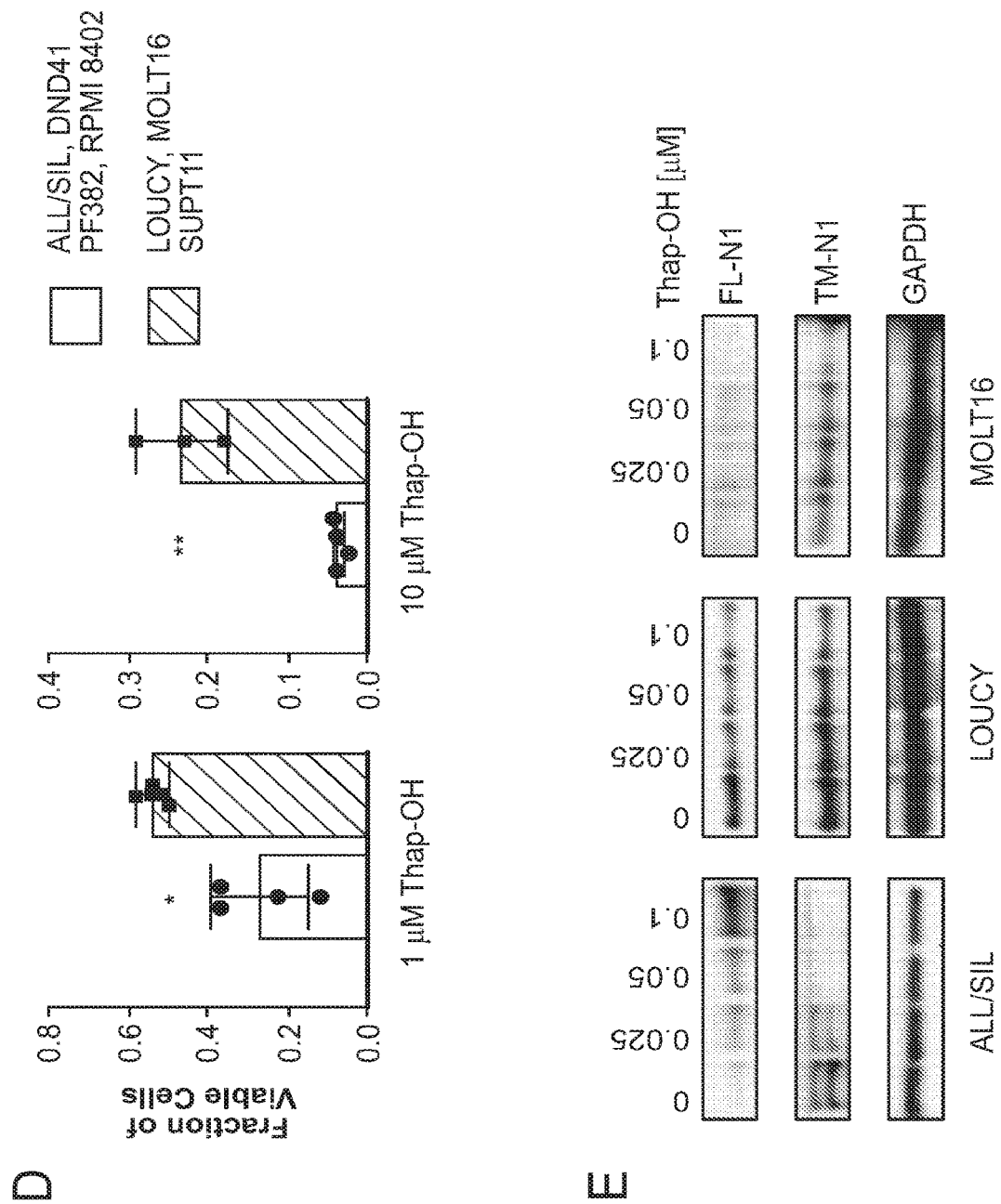
FIG. 9, continued

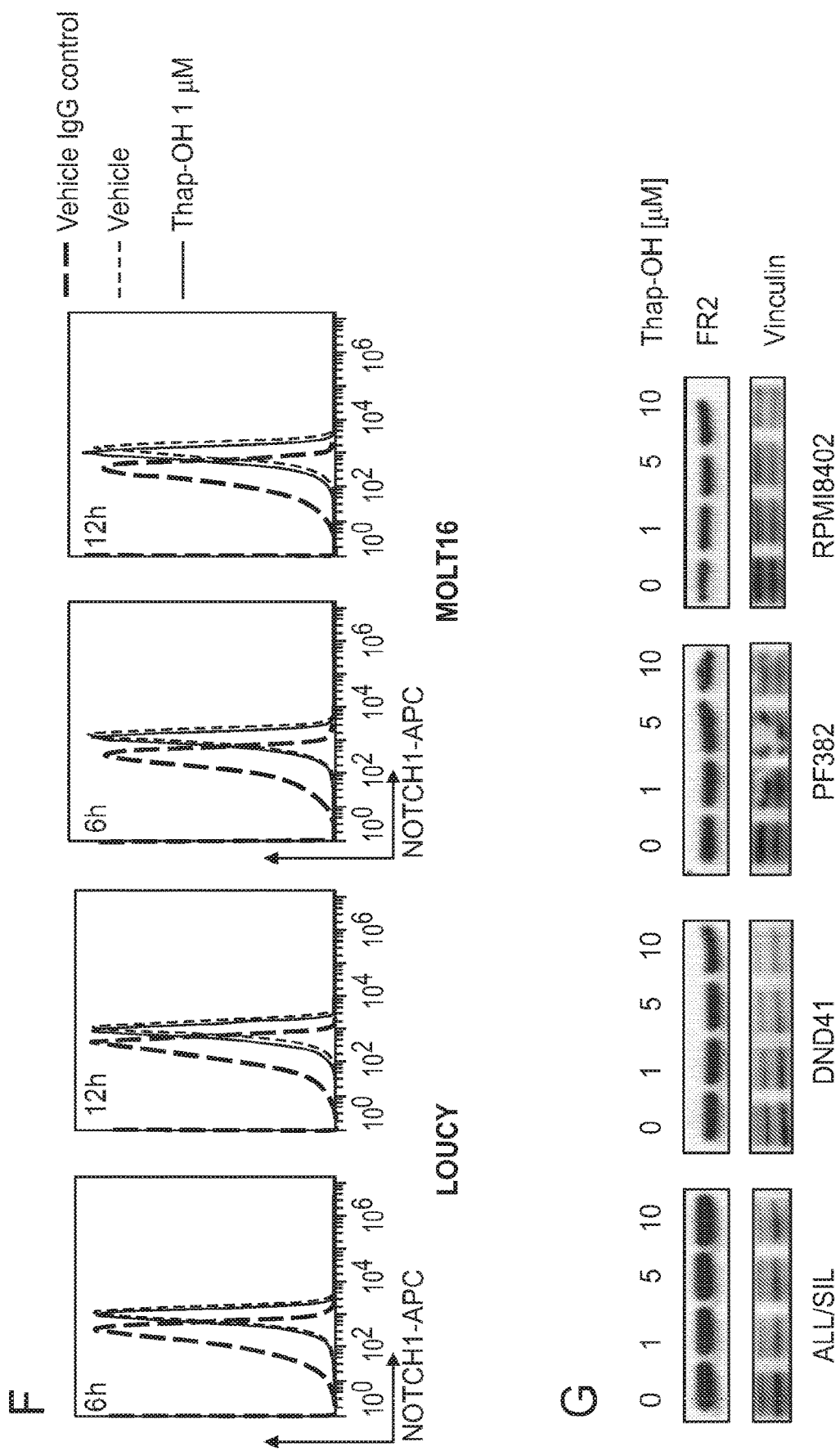
FIG. 9, continued

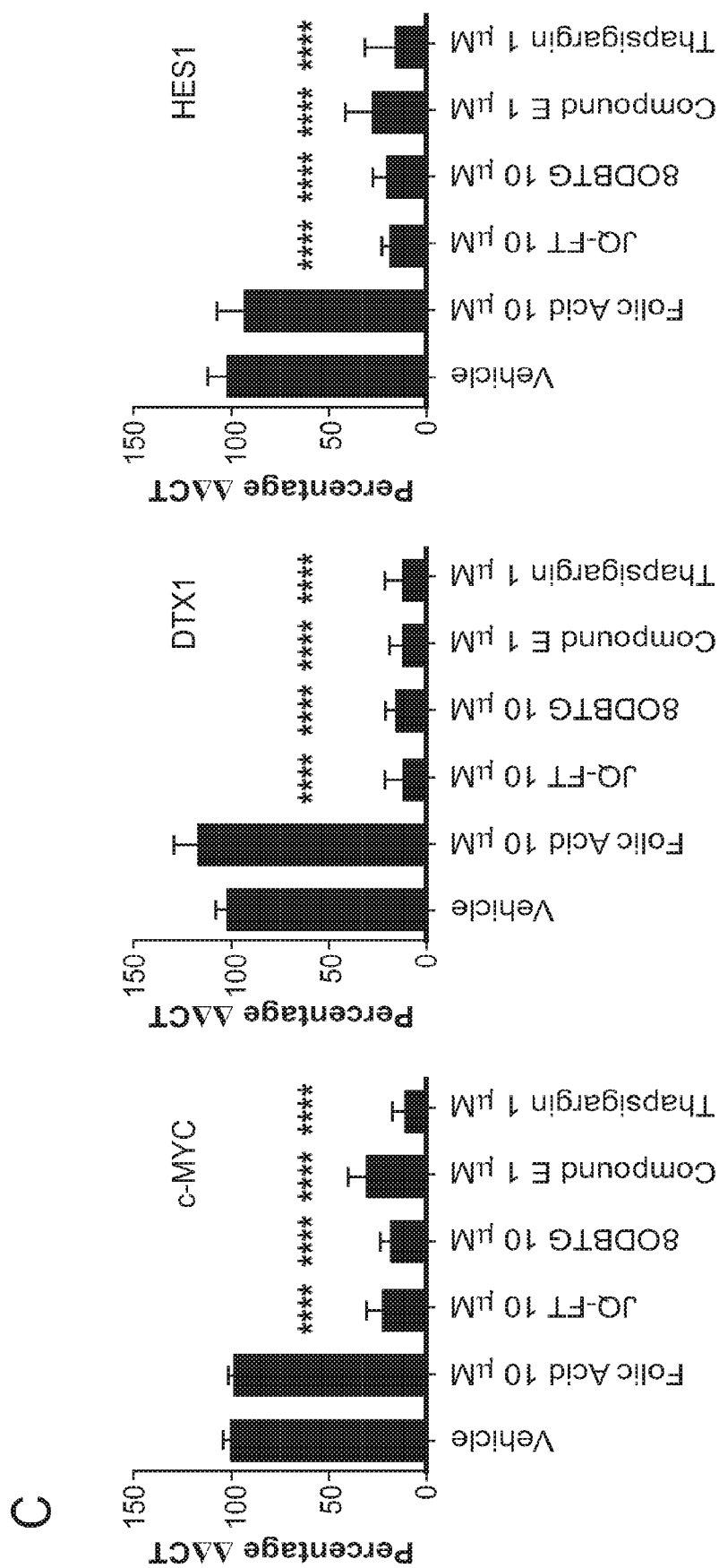
FIG. 10, continued

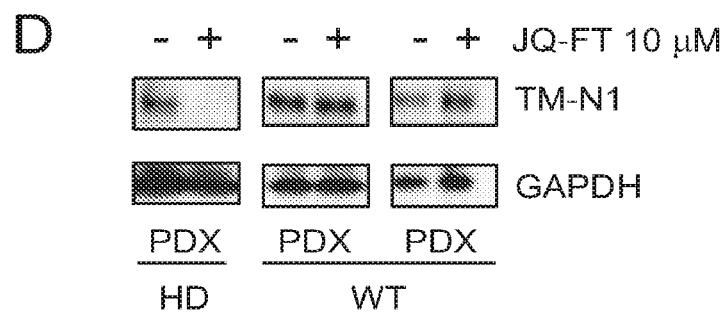
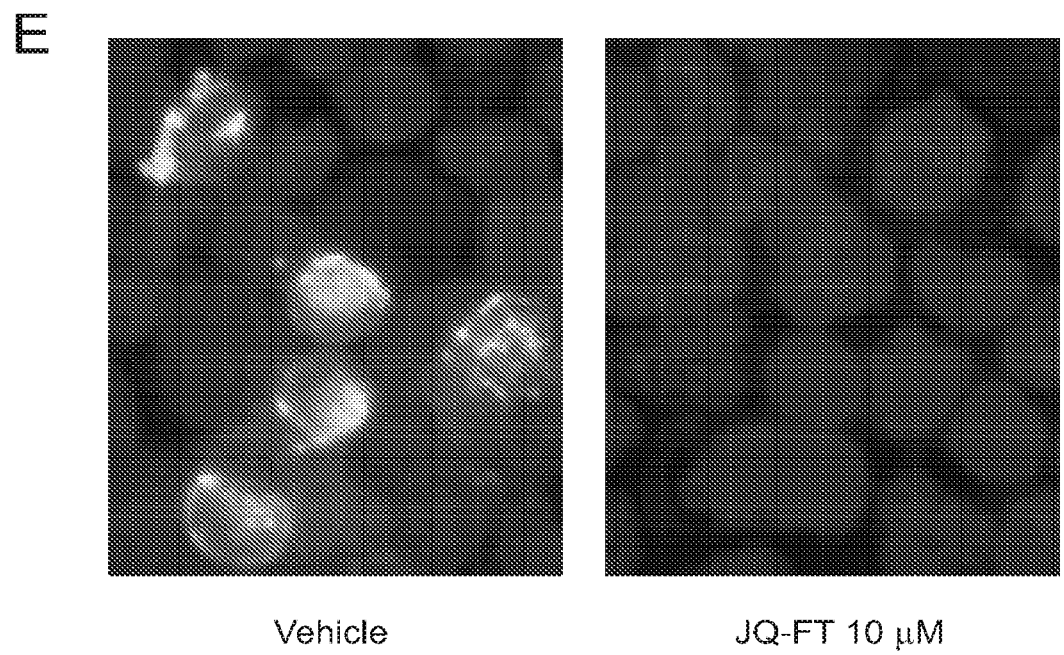
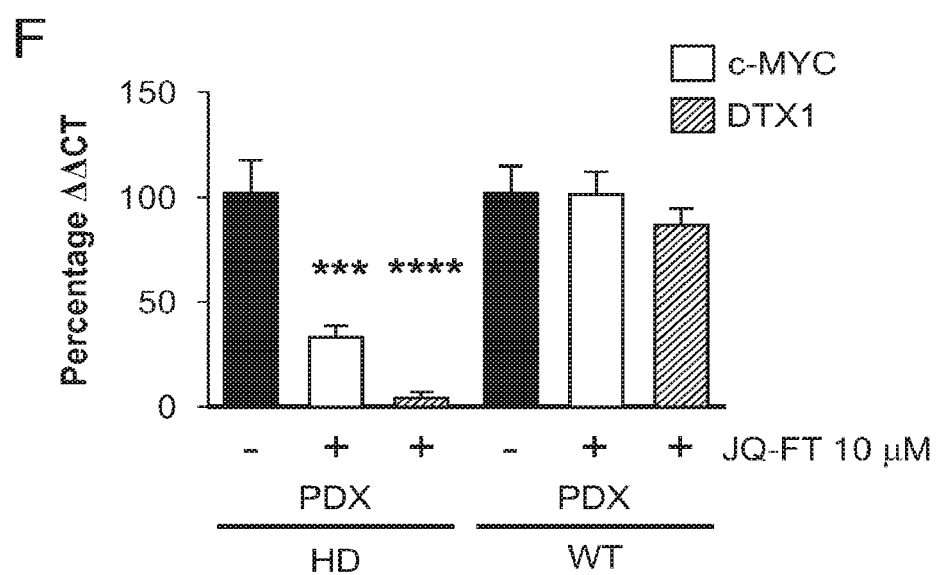
FIG. 10, continued

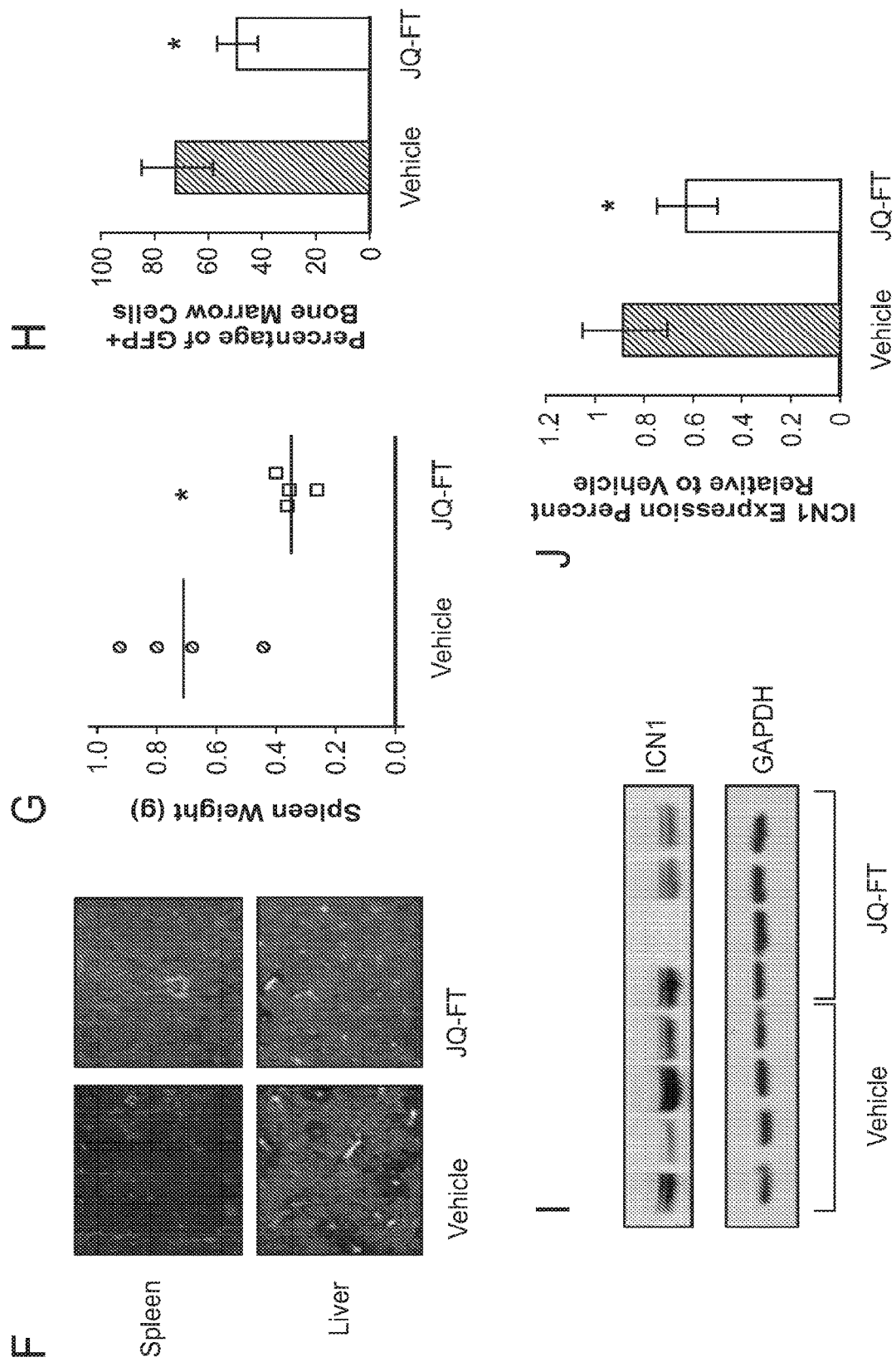
FIG. 11, continued

FOLATE-CONJUGATED MOLECULES FOR DELIVERY OF TOXIC SMALL MOLECULE INHIBITORS TO CANCER CELLS AND METHODS OF USE

RELATED APPLICATIONS

This application is the U.S. national phase of International Patent Application No. PCT/US2015/59222, filed Nov. 5, 2015, which claims the benefit of priority to U.S. Provisional Patent Application Ser. No. 62/075,615, filed Nov. 5, 2014, the entire contents of each of which are hereby incorporated by reference in their entireties.

BACKGROUND

Thapsigargin (TG) is a naturally-occurring compound that is highly specific for inhibiting the sarco/endoplasmic reticulum and endoplasmic reticulum $Ca^{2+}$-ATPase pump (SERCA). The inventors recently identified TG as a modulator of Notch (Roti G., et al., "Complementary genomic screens identify SERCA as a therapeutic target in NOTCH1 mutated cancer." Cancer Cell, 2013, 23(3):390-405.). The inhibition of SERCA leads to Notch inactivation, which inhibits T-cell acute lymphoblastic leukemia (T-ALL) growth both in vitro and in vivo. However, inhibition of the SERCA pump induced by TG leads to an initial depletion of the endoplasmic reticulum (ER) $Ca^{2+}$ pool, which ultimately results in on increase in intracellular calcium. Therefore, prolonged exposure to TG could induce apoptosis in a variety of rapidly proliferating cell types in vitro. Thapsigargin is able to kill proliferatively quiescent G0 cells, but is non-specific for any cell types. Therefore, it is difficult to administer and deliver TG systemically due to significant nonspecific host toxicity (e.g., cardiac toxicity). Therefore, there remains a need to develop methods for selectivity delivering to rapidly proliferating cells a composition having the toxicity and activity of thapsigargin.

SUMMARY OF THE INVENTION

In certain embodiments, the invention provides a compound, comprising a pharmacophore having the structure of formula (I):

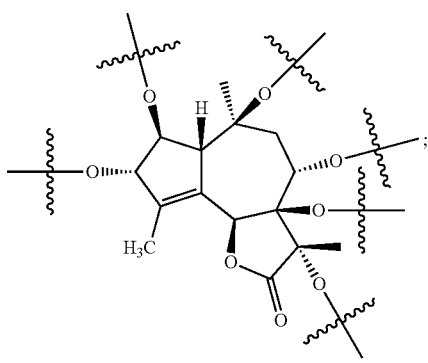

(I)

and a cell-targeting ligand moiety, wherein the pharmacophore and the cell-targeting ligand moiety are covalently linked.

In certain embodiments, the cell-targeting ligand moiety binds to a receptor expressed on the surface of a cell. In certain embodiments, the receptor is a folic acid receptor or a CD19 receptor.

In certain embodiments, the cell-targeting ligand moiety is covalently linked to the pharmacophore through a linking moiety. In certain embodiments, the linking moiety comprises one or more bonds that are cleavable under physiologic conditions. The one or more bonds cleavable under physiological conditions can include moieties such as amide, carbonate, carbamate, ether, ester, disulfide, sulfonate ester, sulfonamide, acetal, and/or ketal.

In certain embodiments, the cell-targeting ligand moiety comprises a residue of folic acid or a residue of an antibody.

In certain embodiments, the cell-targeting ligand moiety is cleaved from the pharmacophore after the compound is delivered to a cell.

In certain embodiments, the compound has the structure of formula (II):

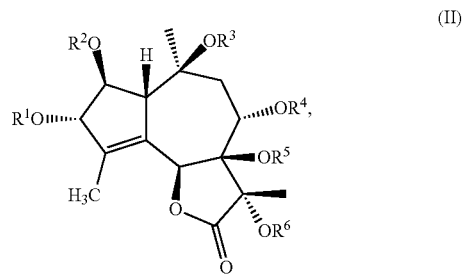

(II)

or a pharmaceutically acceptable salt thereof;

wherein $R^1$, $R^2$, $R^3$, $R^4$, $R^5$, and $R^6$, independently for each occurrence, comprises a cell-targeting ligand moiety, or is H, (CO)hydrocarbyl, COOH, hydrocarbyl, (CO)(NH)hhydrocarbyl, or (CO)O-hydrocarbyl; and wherein at least one of $R^1$, $R^2$, $R^3$, $R^4$, $R^5$, and $R^6$ comprises a cell-targeting ligand moiety.

In certain embodiments, the $R^1$, $R^2$, $R^3$, $R^4$, $R^5$, or $R^6$ that comprises a cell-targeting ligand moiety further comprises a linking moiety.

In certain embodiments, $R^1$, $R^2$, $R^3$, $R^4$, $R^5$, and $R^6$, independently for each occurrence, comprises a cell-targeting ligand moiety, or is H or (CO)hydrocarbyl.

In certain embodiments, $R^4$ comprises a residue of folic acid.

In certain embodiments, the compound has the structure of formula (III),

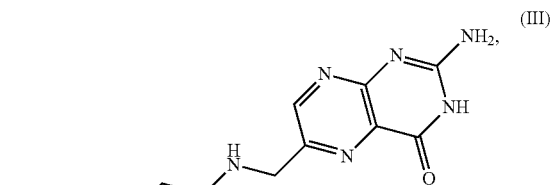
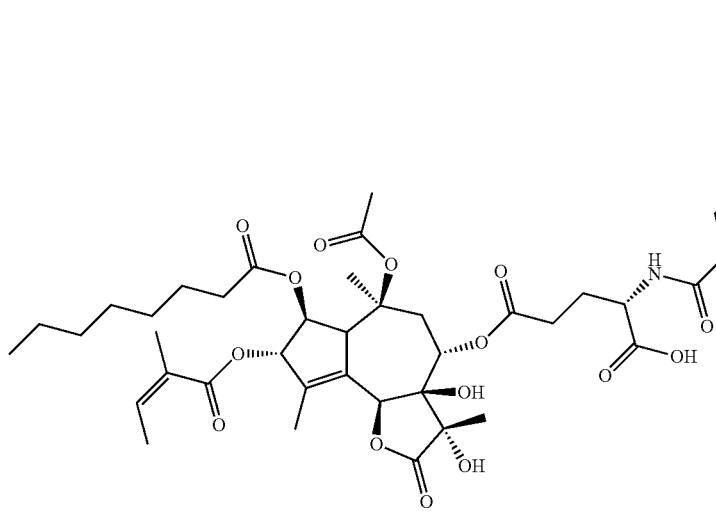

or a pharmaceutically acceptable salt thereof.

The invention also provides pharmaceutical compositions comprising a compound of any one of formulae (I), (II), or (III), and a pharmaceutically acceptable excipient.

The invention also provides methods of treating cancer, comprising administering to a patient in need thereof a therapeutically effective amount of a compound of any one of formula (I), (II), or (III).

In certain embodiments, the cancer comprises cancer cells over-expressing a folic acid receptor. In certain embodiments, the cancer is characterized by aberrant activity of the NOTCH1 gene. In certain embodiments, the cancer is ovarian cancer, non-small cell lung cancer, breast cancer, multiple myeloma, chronic lymphocytic leukemia (CLL), acute lymphoblastic leukemia (ALL), B-cell lymphoma, medulloblastoma, colorectal cancer, or melanoma.

In certain embodiments, the methods of treating cancer further comprise administration of an additional chemotherapeutic agent.

In certain embodiments, the subject is a mammal, for example a human.

The invention further provides methods of inhibiting activation of NOTCH1, comprising contacting NOTCH1 with an amount of a compound of any one formulae (I), (II), or (III) effective to inhibit NOTCH1.

BRIEF DESCRIPTION OF THE DRAWINGS

FIG. 2, panel A is a bar graph showing that cells treated with the indicated dose of compounds for 24 h demonstrate accumulation of FL-Notch1 with reduced TM-NOTCH1. FIG. 2, panel B is a graph showing that Folate-Thap causes a loss of Notch in a manner similar to thapsigargin as measured by flow cytometry. FIG. 2, panel C shows that Folate-Thap causes arrest of cell proliferation.

FIG. 3, panel A is an LCMS trace used to identify the existence of Thap-OH in cell lysate. FIG. 3. panel B depicts the structures of folate-TAMRA and folate-FITC. FIG. 3, panel C is a graph showing folate-FITC uptake dose-dependency. FIG. 3, panel D demonstrates that free folic acid competes with folate-FITC.

DETAILED DESCRIPTION OF THE INVENTION

Figure 1:
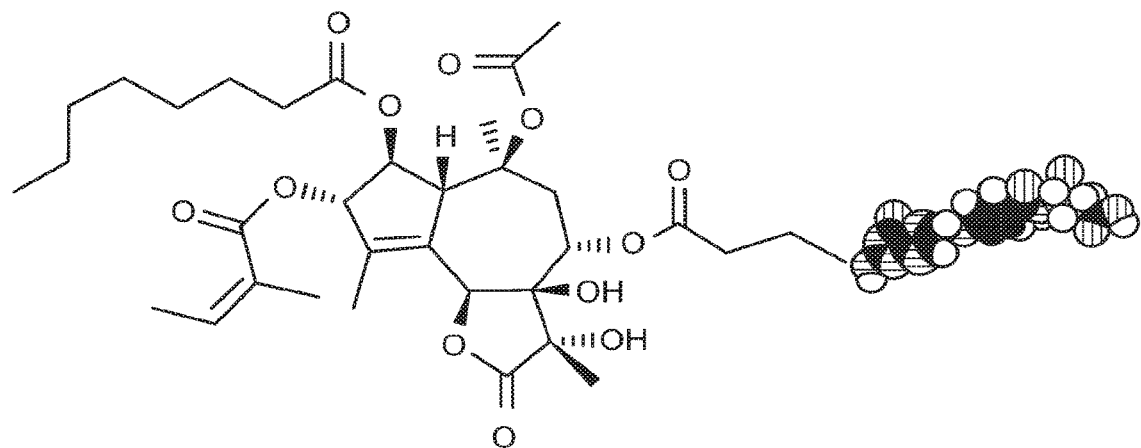
FIG. 1 shows the design principle of folate-based drug delivery.
Figure 1:
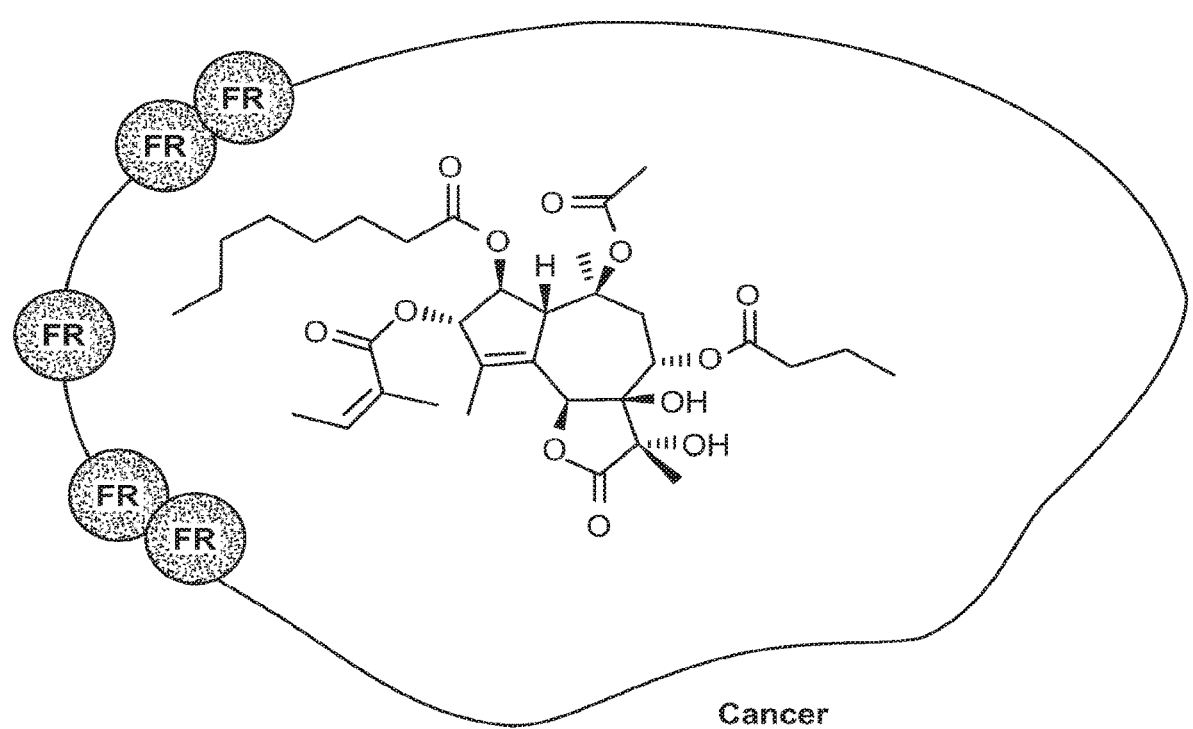

Thapsigargin is a highly specific inhibitor of sarco/endoplasmic reticulum and endoplasmic reticulum $Ca^{2+}$-ATPase pump (SERCA) and the Notch signaling pathway. However, thapsigargin also exhibits non-specific toxicity in various ceil types. The present invention is based, at least in part, on the discovery that chemical modification of thapsigargin yields compounds that selectively target certain cells, and in those cells can successfully impair the activation of the Notch signaling pathway, and also minimize the systemic toxicity observed for thapsigargin. This discovery can be of use in the treatment of diseases that rely on the Notch signaling pathway, such as certain cancers.

I. Definitions

The articles "a" and "an" are used herein to refer to one or to more than one (i.e., to at least one) of the grammatical object of the article. By way of example, "an element" means one element or more than one element.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen an one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained, or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkythio, a sulfate, a sulfonate, a sulfamoyl, a sulfonamide, a sulfonyl, a heterocycyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkythio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such, substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

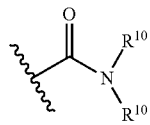

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

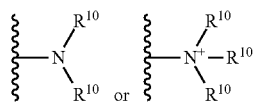

wherein each $R^{10}$ independently represents a hydrogen or a hydrocarbyl group, or two $R^{10}$ are taken together with the N atom to which they are attached complete a heterocycle having from 4 to 8 atoms in the ring structure. In certain embodiments, amine encompasses cyclic amines, including bicyclic amines. In certain embodiments, amine includes DABCO (1,4-diazabicyclo[2.2.2]octane).

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

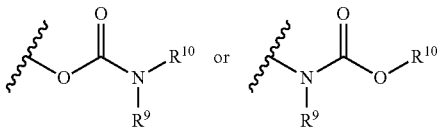

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkane rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclop [2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1 H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$ H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond, and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heroalyls, and/or heterocycly(s) in which two or more atoms are common to two adjoining rings, e.g., the rings are "fused rings". Each of the rings of the polycyclic can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone, it will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

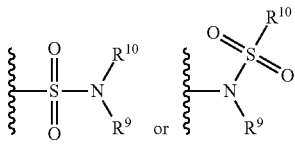

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl. In certain embodiments, the sulfoxide may be a stereogenic center. In certain such embodiments, the compounds may be enriched for one isomer of the sulfoxide.

The term "sulfonate" is art-recognized and refers to the group SO$_3$H, or a pharmaceutically acceptable salt thereof. A sulfonate ester refers to a group —S(O)$_2$—OR$^{10}$, wherein $R^{10}$ represents a hydrocarbyl.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein $R^{10}$ represents a hydrocarbyl.

The term "thioether", as used herein, is equivalent to an ether, wherein the oxygen is replaced with a sulfur.

The term "disulfide" refers to a group —S—S—$R^{10}$, wherein $R^{10}$ represents a hydrocarbyl.

The term "urea" is art-recognized and may be represented by the general formula

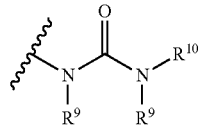

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed, 1999, John Wiley & Sons, NY and Harrison et al., *Compendium of Synthetic Organic Methods*, Vols, 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region: (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc Natl. Acad. Sci. USA* 85:5879-5883; and Osbourn et al. 1998, Nature Biotechnology 16; 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Antibodies may be polyclonal or monoclonal; xenogeneic, allogeneic, or syngeneic; or modified forms thereof (e.g., humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain rumor testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease In certain embodiments, the cancer is characterized by aberrant activity of the NOTCH1 gene or the Notch signaling pathway. In certain embodiments, the cancer is ovarian cancer, non-small cell lung cancer, breast cancer, multiple myeloma, chronic lymphocytic leukemia (CLL), acute lymphoblastic leukemia (ALL), B-cell lymphoma, medulloblastoma, colorectal cancer, or melanoma.

The term "gene expression data" or "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a tumor or biopsy sample. Gene expression data and gene expression levels can be stored on computer readable media, e.g., the computer readable medium used in conjunction with a microarray or chip reading device. Such gene expression data can be manipulated to generate gene expression signatures.

As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented.

The term "modulate" includes up-regulation and down-regulation, e.g., enhancing or inhibiting a response.

The term "subject" refers to any healthy animal, mammal or human, or any animal, mammal or human afflicted with a condition of interest (e.g., cancer). The term "subject" is interchangeable with "patient." In other embodiments, the subject has ovarian cancer, non-small cell lung cancer, breast cancer, multiple myeloma, chronic lymphocytic leukemia (CLL), acute lymphoblastic leukemia (ALL), or B-cell lymphoma.

II. Conjugates of the Invention

The invention provides compounds that comprise a pharmacophore derived from thapsigargin and a ligand for a cell surface receptor that can selectively target cancer cells and induce apoptosis via inhibition of the Notch signaling pathway (FIG. 1).

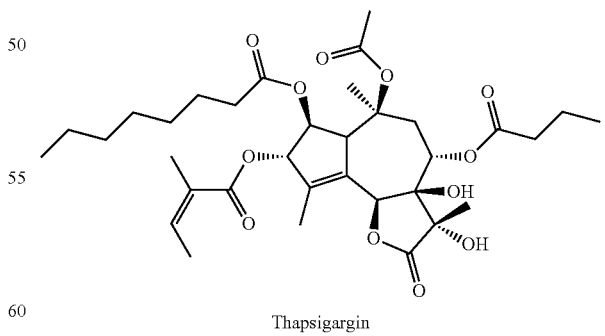

Thapsigargin

In certain embodiments, the invention provides a compound comprising a pharmacophore of formula (I) and a cell-targeting ligand moiety, wherein the pharmacophore and the cell-targeting ligand moiety are covalently linked, and where formula (I) is represented by:

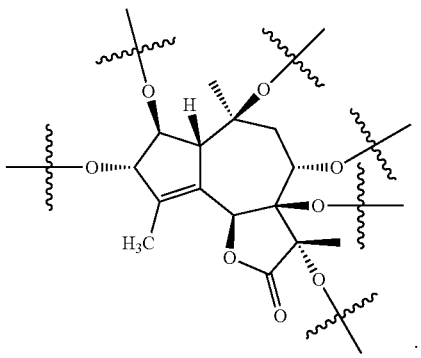

(I)

In certain embodiments, the pharmacophore derived from thapsigargin has the structure of formula (I), wherein the wavy bond represents sites where the pharmacophore may be derivatized by the cell-targeting ligand moiety. The pharmacophore may relate to the parent structure of thapsigargin via truncation at, for example, any hydrolyzable bond present in the parent structure, such as an ester bond.

Formula (I) depicts one stereochemical isomer of the pharmacophore included in the compounds of the invention. However, the pharmacophore derived from thapsigargin farther encompasses enantiomers, diastereomers, and epimers of the pharmacophore depicted in formula (I).

The pharmacophore of formula (I) may be covalently linked to one, two, or more cell-targeting ligand moieties. In certain embodiments, one cell-targeting ligand moiety is covalently linked to the pharmacophore of formula (I) at two different positions on the pharmacophore, as allowable by valence and molecular geometry.

In certain embodiments, the compounds of the invention provide pro-drug forms of thapsigargin and thapsigargin derivatives.

In certain embodiments, the cell-targeting ligand moiety binds to a receptor expressed on the surface of a cell. In certain embodiments, the receptor expressed on the surface of the cell is particular to a certain cell type, or is over-expressed in a certain cell type. A cell type associated with a disease or disorder, for example, a cancer, can express a receptor at a higher level than other cell types. Accordingly, the ligand-receptor recognition interaction can enable cell-selective drug delivery.

Figure 4:
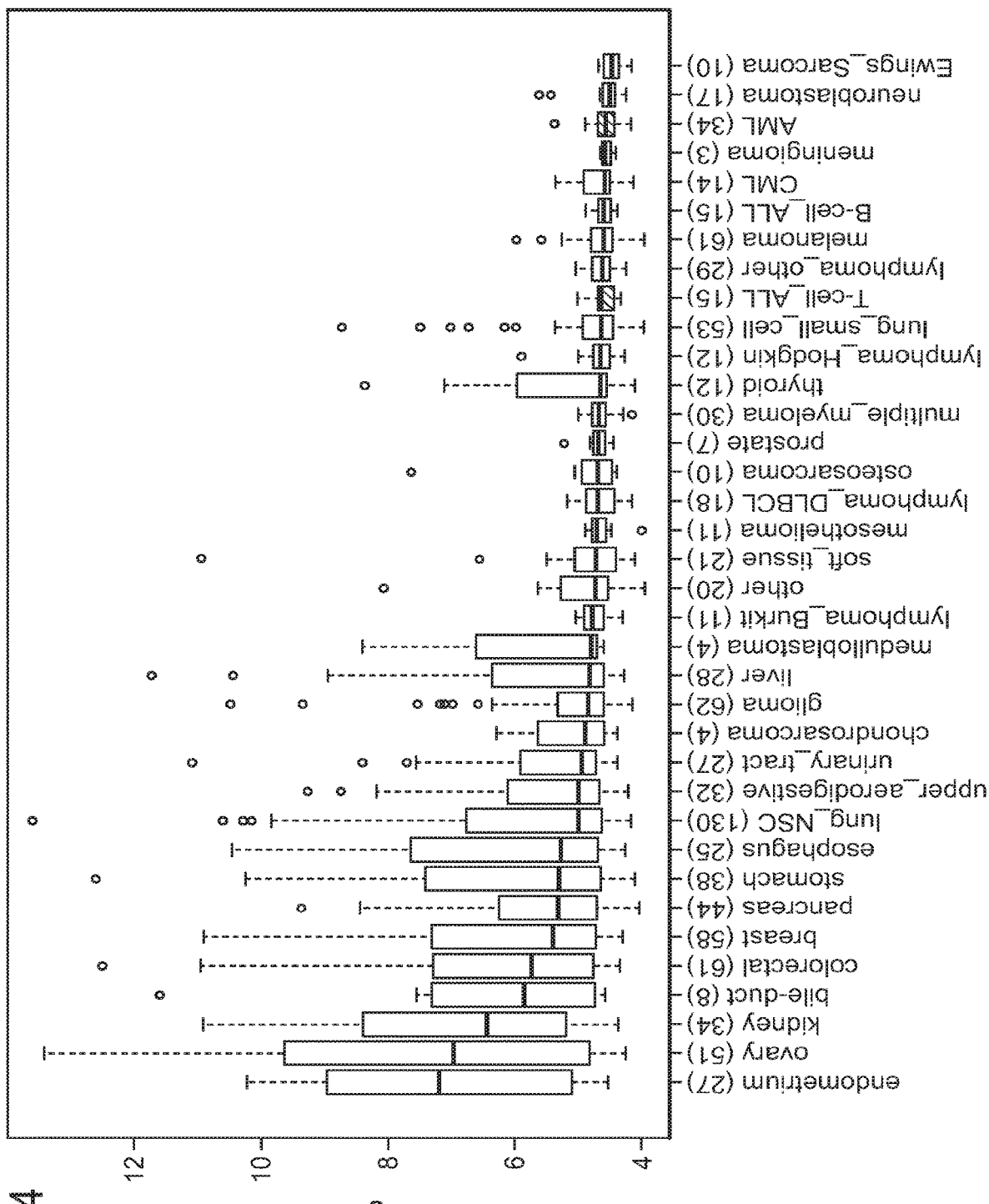
FIG. 4 shows CCLE data for the expression of FOLR1 in various cell lines.

Exemplary receptors that can bind to the ligand moiety include folate receptors and CD19 receptors. Folate receptors include four different isoforms of the receptor. In certain embodiments, the compounds of the invention target FR1 (α)-2(β). Folate receptors may be over-expressed in certain cancers, such as in ovarian cancer cells. For example, data supports that the folate receptors are expressed in the majority of non-mucinous epithelial ovarian tumors at levels that are 10- to 100-fold higher than the normal expression of the folate receptor in the kidney, lung, and breast epithelial cells (FIG. 4). Therefore, the compounds of the invention are advantageous due to their specificity toward cancer cells in the presence of normal cells, minimizing systemic toxicity.

In certain embodiments, the receptor is a folic acid receptor or a CD19 receptor.

In certain embodiments, the cell-targeting ligand moiety is covalently linked to the pharmacophore through a linking moiety. In certain embodiments, the linking moiety comprises one or more bonds that are cleavable under physiologic conditions. The one or more bonds cleavable under physiologic conditions can include moieties such as amide, carbonate, carbamate, ether, ester, disulfide, sulfonate ester, sulfonamide, acetal, ketal, or other acid- or base-labile bonds. In certain embodiments, two substitutable positions of the pharmacophore, for example adjacent substitutable positions, are each covalently bound to a linking moiety, which in turn covalently links the pharmacophore to a cell-targeting ligand moiety.

In certain embodiments, the cell-targeting ligand moiety comprises a residue of folic acid or a residue of an antibody.

In certain embodiments, the pharmacophore derived from thapsigargin can be chemically modified by a residue of biotin. In certain embodiments, the pharmacophore is covalently bound to a residue of biotin. In certain such embodiments, the compound can be referred to herein as "biotinylated thap". In certain embodiments, the biotinylated thap is useful in chemical sequencing.

In certain embodiments, the residue of folic acid is folic acid, substituted by a linking moiety at any substitutable position (e.g., —NH$_2$, —NH, COOH), valence permitting. In certain embodiments, the residue of folic acid is folic acid, substituted by a linking moiety at either of the carboxylic acid moieties. In certain embodiments, the residue of folic acid is folic acid, substituted by a linking moiety at the terminal carboxylic acid moiety.

In certain embodiments, the antibody is an anti-immunoglobulin antibody, or any other antibody as described herein.

In certain embodiments, the cell-targeting ligand moiety is cleaved from the pharmacophore after the compound is delivered to a cell. For example, the conjugate can target a cell-surface receptor, be taken into the cell via endocytosis, and then the cell-targeting ligand moiety can be cleaved from the conjugate, releasing the pharmacophore. In certain embodiments, the pharmacophore, once released from the conjugate, is an active drag residue. In certain embodiments, the cleavage is a result of the pH of the cytoplasmic matrix.

In certain embodiments, the cell-targeting ligand moiety is cleaved from the pharmacophore via cleavage of one or more bonds in the linking moiety. For example, under physiological conditions, bonds such as disulfide bonds, amide linkages, and ester linkages may cleave or hydrolyze, thus separating the pharmacophore from the cell-targeting ligand moiety.

In certain embodiments, the compound of the invention has the structure of formula (II):

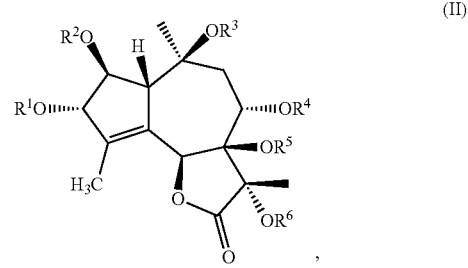

(II)

or a pharmaceutically acceptable salt thereof:
wherein $R^1$, $R^2$, $R^3$, $R^4$, $R^5$, and $R^6$, independently for each occurrence, comprises a cell-targeting ligand, moiety, or is H, (CO)hydrocarbyl, COOH, hydrocarbyl, (CO)(NH)hydrocarbyl, or (CO)O-hydrocarbyl; and
wherein at least one of $R^1$, $R^2$, $R^3$, $R^4$, $R^5$, and $R^6$ comprises a cell-targeting ligand moiety.

Formula (II) depicts one stereochemical isomer of the pharmacophore included in the compounds of the invention. However, the pharmacophore derived from thapsigargin further encompasses enantiomers, diastereomers, and epimers of the pharmacophore depicted in formula (II).

In certain embodiments, the $R^1$, $R^2$, $R^3$, $R^4$, $R^5$, or $R^6$ that comprises a cell-targeting ligand moiety further comprises a linking moiety.

In certain embodiments, $R^1$, $R^2$, $R^3$, $R^4$, $R^5$, and $R^6$, independently for each occurrence, comprises a cell-targeting ligand moiety, or is H or (CO)hydrocarbyl.

In certain embodiments, (CO)hydrocarbyl includes (CO)($C_1$-$C_{10}$)alkyl or (CO)($C_1$-$C_{10}$)alkenyl.

In certain embodiments, one or more of $R^1$, $R^2$, $R^3$, $R^4$, $R^5$, or $R^6$ comprises a residue of folic acid. In certain embodiments, one of $R^1$, $R^2$, $R^3$, $R^4$, $R^5$, or $R^6$ comprises a residue of folic acid. In certain embodiments, $R^4$ comprises a residue of folic acid. In certain embodiments, $R^4$ comprises a residue of folic acid and a linking moiety.

Exemplary compounds provided by the invention include compounds of formulae (III), (IV), (V), (VI), (VII), (VIII), or (IX);

wherein formula (III) is represented by:

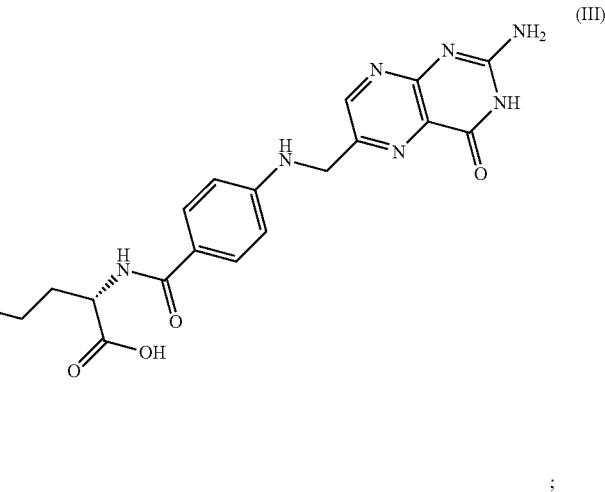
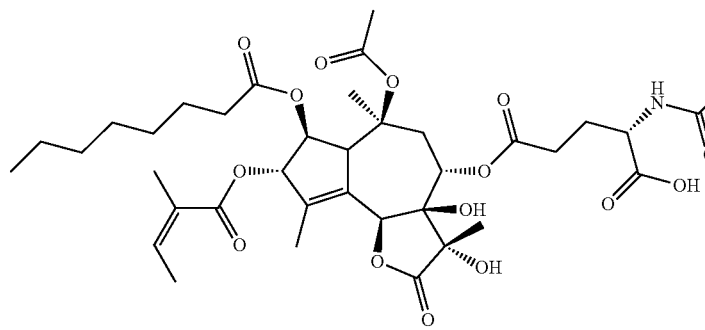

;

wherein formula (IV) is represented by:

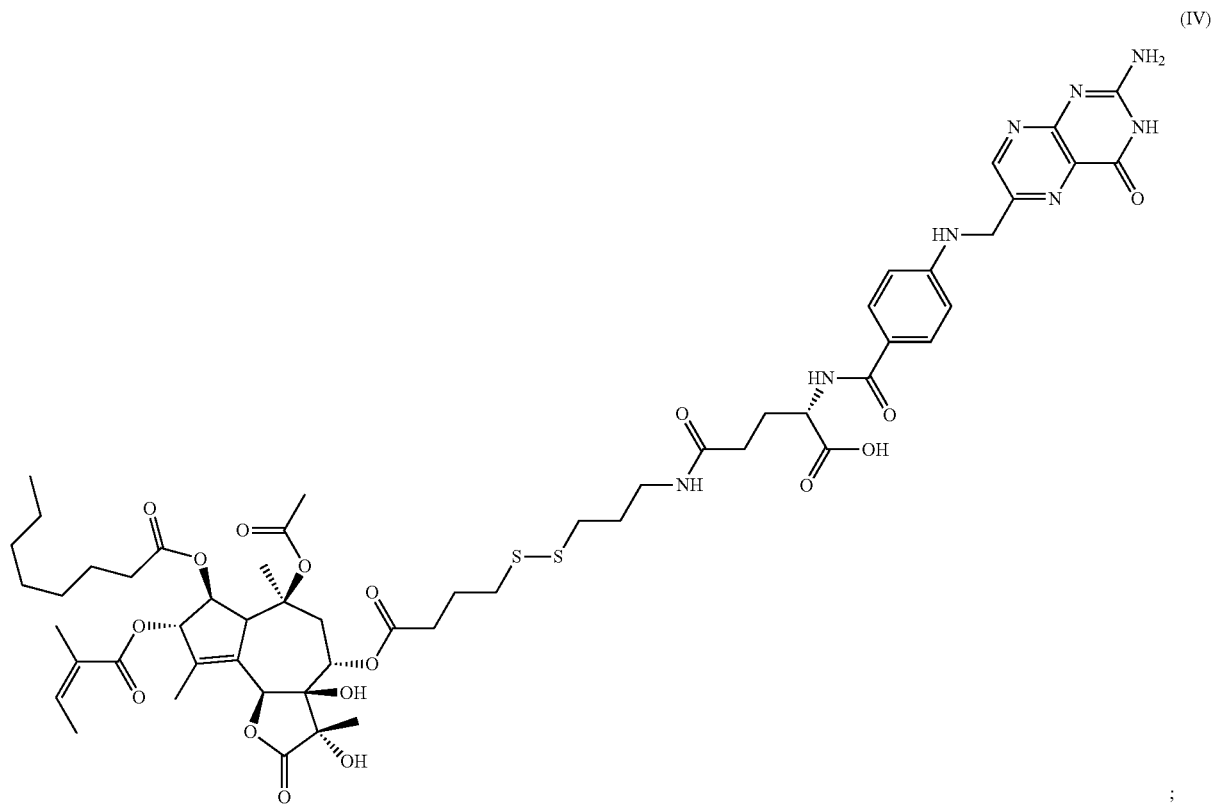 [SMILES: C/C=C(/C)C(=O)O[C@H]1C(C)=C2C([C@@H]1OC(=O)CCCCCCC)[C@@](C)(OC(C)=O)C[C@H](OC(=O)CCCSSCCCNC(=O)CC[C@H](NC(=O)c1ccc(NCc3cnc4nc(N)[nH]c(=O)c4n3)cc1)C(=O)O)[C@@]1(O)[C@H]2OC(=O)[C@@]1(C)O]

;

wherein formula (V) is represented by:
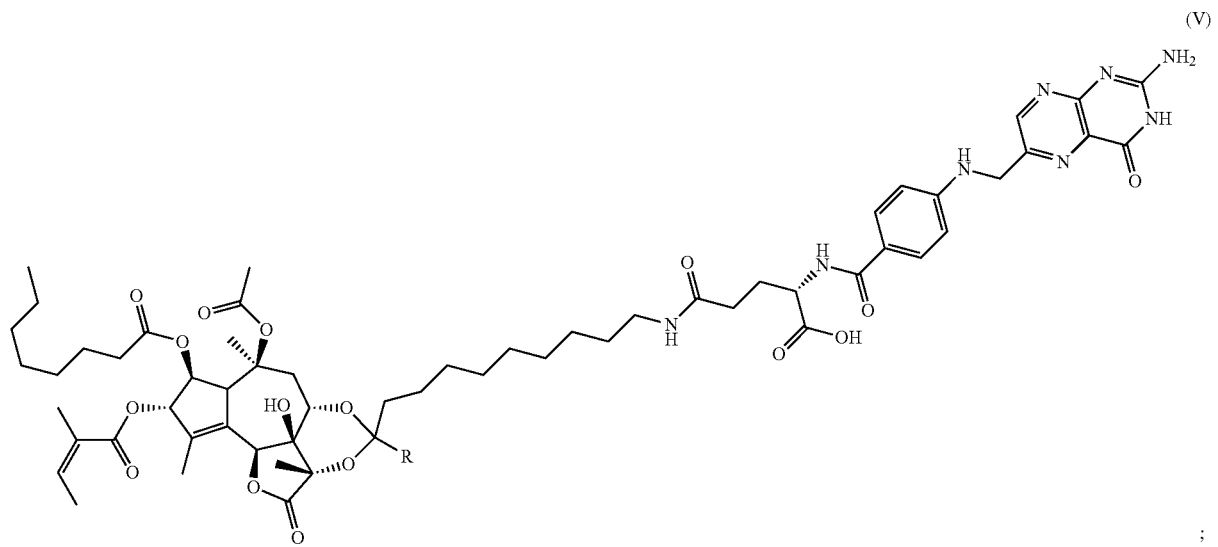
;
wherein formula (VI) is represented by:
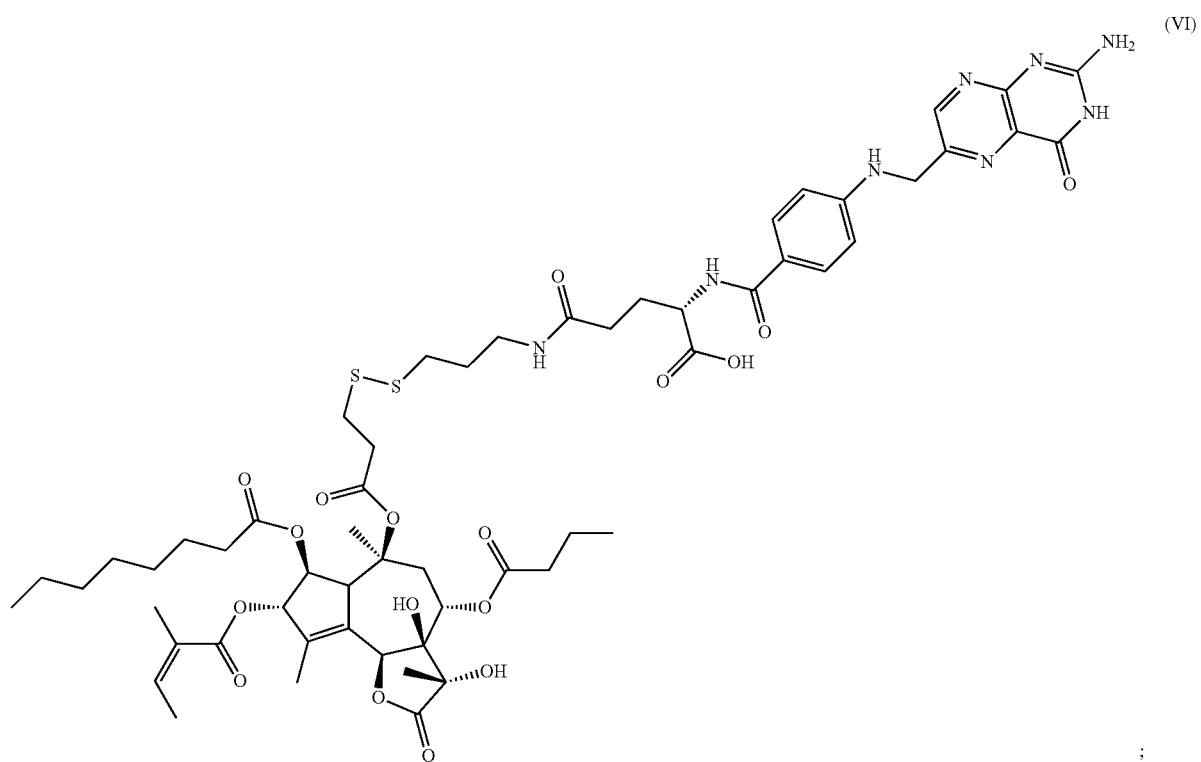
;

wherein formula (VII) is represented by:

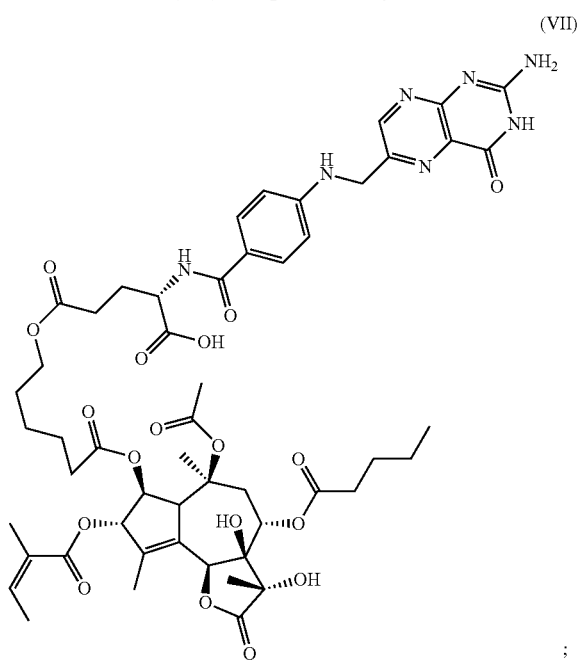

(VII)

wherein formula (VIII) is represented by:

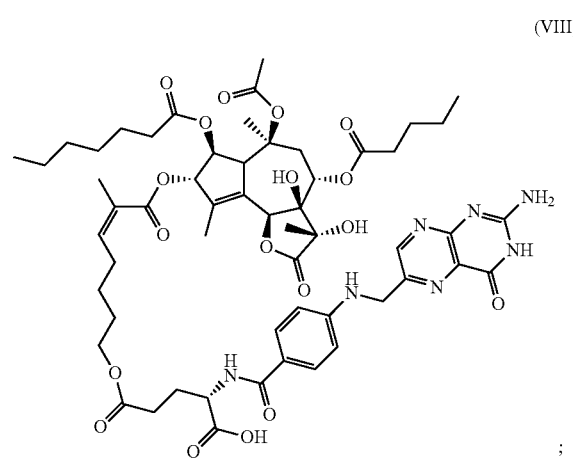

(VIII)

;

and
wherein formula (IX) is represented by:

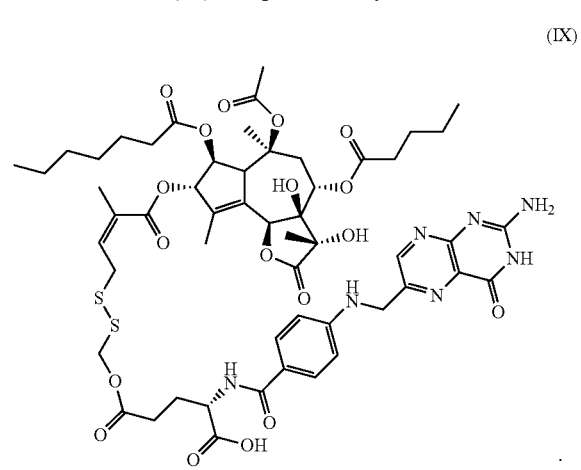

(IX)

III. Pharmaceutical Compositions of the Conjugate

In certain embodiments, the invention also provides pharmaceutical compositions, comprising a compound of the invention and a pharmaceutically acceptable excipient.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs.

In certain embodiments, the composition is a form suitable for injection, systemic administration, or topical administration. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch.

The composition can also be present in a solution or suspension suitable for topical administration. The topically applicable form of the composition can a transdermal patch, ointment, cream, gel, suspension, liquid, elixir, or eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid earners, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, grannies and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid: (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrafuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for administration to the mouth may be presented as a mouthwash, or an oral spray, or an oral ointment.

Formulations of the pharmaceutical compositions for rectal, vaginal, or urethral administration may be presented as a suppository, which may be prepared by mixing one or snore active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Alternatively or additionally, compositions can be formulated for delivery via a catheter, stent, wire, or other intraluminal device. Delivery via such devices may be especially useful for delivery to the bladder, urethra, ureter, rectum, or intestine.

Dosage forms for the topical administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

IV. Methods of Using the Conjugates of the Invention

In the last decade, NOTCH1 has been identified as one of the most frequently mutated genes across all cancers. In hematologic malignancies, activating NOTCH1 mutations are observed in chronic lymphocytic leukemia (CLL), mantle cell lymphoma, and at an exceptionally high rate in T-ALL, where NOTCH1 mutations represent the most common actionable genetic abnormality. Targeted NOTCH1 therapies, such as gamma-secretase inhibitors and receptor-blocking antibodies have entered early-stage clinical trials. However, these modalities have the liability of inhibiting normal NOTCH1 and NOTCH2. In addition to the known potential for gut toxicity, there is also a significant concern for secondary malignancies as Notch receptors are established context-specific tumor suppressor genes. Thus, the development of tumor-directed inhibitors with selective activity against mutated proteins is highly desirable.

Although inhibition of SERCA proteins to selectively target mutated NOTCH1 with free thapsigargin is promising, thapsigargin is poorly tolerated. The present invention provides improved methods for inhibition of SERCA proteins using a thapsigargin-folate conjugate.

The present invention provides methods of small-molecule folate-mediated delivery of thapsigargin to enable selective and target-specific drug delivery to T-ALL cells. In certain embodiments, the inhibitor, thapsigargin, is connected to folic acid with a cleavable bond and is transferred into the cell after binding to FR on the cell surface. The expression of FR in T-ALL enabled the selective recognition of the designed molecule, JQ-FT by cancer cells. The cleavable bond feature of the molecule facilitated direct delivery of the inhibitory motif to the target (SERCA) and subsequently blocked mutant NOTCH1 maturation. This strategy avoided complicated manufacturing processes, such as drug-antibody conjugation, but still allowed selective delivery to the cancer cell. Indeed, the MTD of JQ-FT in mice was 150 fold above thapsigargin, supporting the more selective uptake of the derivatized product. Importantly, in our in vivo experiments, mice were not restricted to a low folate chow to demonstrate FR-mediated antitumor effect in vivo. Such a strategy had been reported in previously published preclinical studies testing folate-drug conjugates. JQ-FT treatment with a low folate diet is expected to have even greater efficacy in vivo.

The present invention enhances the therapeutic window of thapsigargin as a NOTCH1 inhibitor providing dual selectivity; leukemia over normal cell and NOTCH1 mutated over WT receptors, Given the important role of mutations in NOTCH1 in many cancers, JQ-FT offers a potential strategy in treating other tumors with NOTCH1 mutations, such CLL and non-small cell lung cancer. Furthermore, our report demonstrated both in vitro and in vivo that the folic acid-assisted, pathway-specific drug delivery strategy could be an efficient method to solve a common drug delivery problem in the present era of targeted cancer therapy.

Accordingly, in certain embodiments, the invention provides methods of treating cancer, comprising administering to a patient in need thereof a therapeutically effective amount of a compound of the invention that is described herein.

In certain embodiments, the cancer cells targeted by the conjugates of the invention over-express a receptor type. In certain embodiments, the cancer cells express a receptor type at a higher level than non-cancer cell types. In certain embodiments, the cancer cells over-express a folic acid receptor.

In certain embodiments, the cancer is characterized by aberrant activity of the NOTCH1 gene or the Notch signaling pathway.

In certain embodiments, the cancer is ovarian cancer, non-small cell lung cancer, breast cancer, multiple myeloma, chronic lymphocytic leukemia (CLL), acute lymphoblastic leukemia (ALL), B-cell lymphoma, medulloblastoma, colorectal cancer, or melanoma.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed, 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

The methods of the invention further comprise administering to the patient a therapeutically effective amount of an additional chemotherapeutic agent.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The invention further provides methods of inhibiting activation of NOTCH1, comprising contacting NOTCH1 with a compound of the invention described herein in an amount of effective to inhibit NOTCH1.

The invention further provides methods of inhibiting the Notch signaling pathway, comprising contacting a cell with a compound of the invention described herein in an amount of effective to inhibit the Notch signaling pathway.

In certain embodiments, the inhibition of NOTCH1 activation is measured by determining the level of RNA, such as mRNA, of NOTCH1 target genes such as HES1, c-MYC, or DTX1. Alternatively, inhibition may be determined based on the level of a polypeptide or fragment thereof expressed by the gene. In certain embodiments, inhibition of NOTCH1 will be also measured using a complex Notch off signature originally developed by the inventors in a Notch GE-HTS screen. In certain embodiments, NOTCH1 inhibition is measured by flow cytometry. In certain embodiments, NOTCH1 inhibition is measured in heterologous system in which different Notch isoforms can be co-expressed with a specific promoter expressing luciferase.

In certain embodiments, one or more cells are contacted with biotinylated thap under conditions sufficient to inhibit NOTCH1. An antibody targeting biotin can be used to pull down the proteins bound to the thapsigargin derivative (i.e., the "thap" moiety of biotinylated thap). Such proteins can be identified via mass spectrometry. In certain embodiments, methods that identify proteins having an affinity for the thapsigargin derivative are used in the identification of SERCA isoforms that are preferentially inhibited in cancer types such as T-ALL. In certain embodiments, methods that identify proteins having an affinity for the thapsigargin derivative are used in the identification of protein targets for thapsigargin.

EXAMPLES

Example 1

Synthesis of Thapsigargin-Folic Acid Conjugates and Fluorescent Derivatives

Materials and Methods

Reactions were run as described in the individual procedures using standard double manifold and syringe techniques; glassware was dried by baking in an oven at 130° C. for 12 h prior to use. Solvents for reactions were purchased anhydrous from Sigma-Aldrich and used as received. HPLC grade solvents were used for aqueous work ups and chromatography. Reagents were used as received. Reactions were monitored by thin-layer chromatography using EMD silica gel 60 F254 (250-micron) glass-backed plates (visualized by UV fluorescence quenching and staining with $KMnO_4$) and by LC-MS using a Waters Aquity BEH C18 2×50 mm 1.7 μm particle column (50° C.) eluting at 1 mL/min with $H_2O$/acetonitrile [0.2% v/v added formic acid; 95:5 (0 min)→5:95 (3.60 mm)] using alternating positive/negative electrospray ionization (125-1000 amu) and UV detection (210-350 nm). Flash column chromatography was carried out using Merck grade 9385 silica gel 60 Å pore size (230-400 mesh). Melting points were obtained using a capillary melting point apparatus and are uncorrected. $^1$H NMR spectra were recorded at 400 MHz on a Bruker spectrometer and are reported in ppm using the residual solvent signal (dimethylsulfoxide-$d_6$=2.50 ppm; chloroform-d=7.27 ppm; methanol-$d_4$=3.31 ppm; dichloromethane-$d_2$=5.32 ppm) as an internal standard. Data are reported as: {(δ shift), [(s=singlet, d=doublet, dd, doubles: of doublets, ddd=doublet of a dd, t=triplet, quin=quintet, sept=septet, br=broad, ap=apparent), (J=coupling constant in Hz) and (integration]}. Proton-decoupled 13C NMR spectra were recorded at 100 MHz on a Bruker spectrometer and are reported in ppm using the residual solvent signal (chloroform-d=77.0 ppm; dimethylsulfoxide-$d_6$=39.51 ppm; methanol-$d_4$=49.15 ppm) as an internal standard. Infrared spectra were recorded using an ATR-FTIR instrument. High resolution mass spectra were acquired by flow injection on a qTOF Premiere Mass Spectrometer operating in ES+ ionization with resolution ~15,000.

The folate-thapsigargin derivative of the invention was designed based on the following principles: the dual function molecule should actively bind to folate receptor (FR); the connection between folic acid and thapsigargin should be stable in serum but cleaved in the intracellular compartment; and the resulting thapsigargin derivative should potently inhibit SERCA activity. As shown below, the butyl ester bond at C8 was readily and selectively cleaved from the isolated natural product under basic conditions to produce the secondary alcohol, 8-O-debutanoylthapsigargin (Thap-OH). The carboxylate of folic acid was then conjugated to the C8-alcohol of Thap-OH to generate the folate-conjugate JQ-FT.

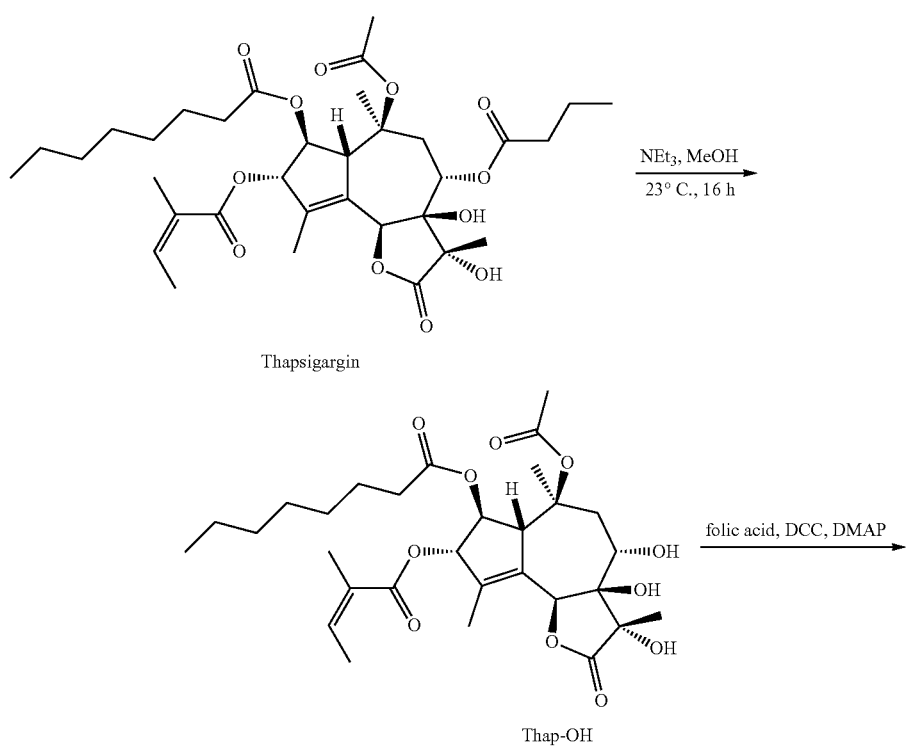

Scheme 1. Synthesis of JQ-FT

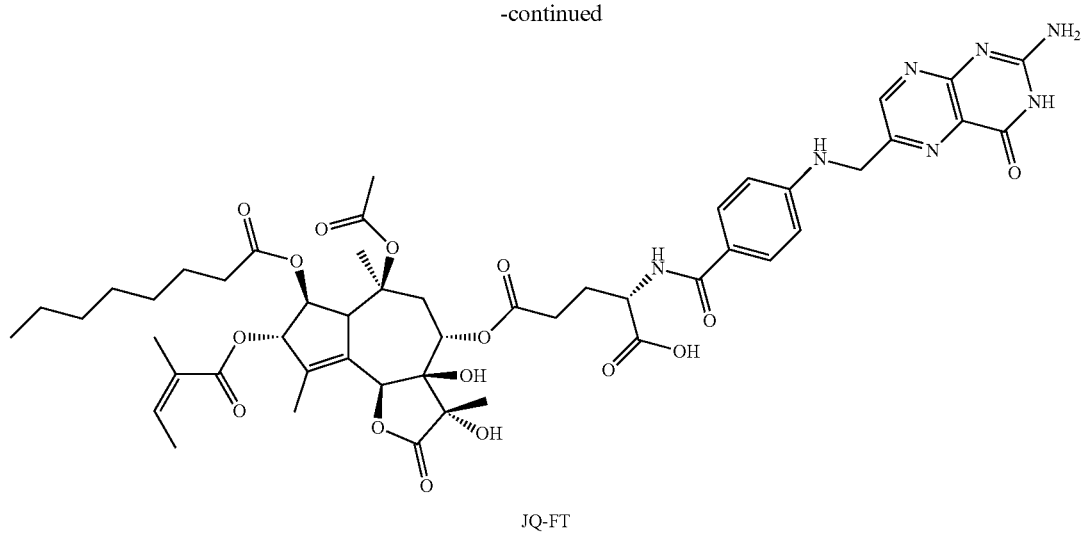

JQ-FT

To a solution of thapsigargin (200 mg, 0.31 mmol) in methanol (4 mL), triethylamine (0.5 mL) was added at 23° C. The resulting clear solution was stirred at 23° C. for 6 h. The solvent was removed in vacuo. The crude reaction was purified directly using column chromatography (MeOH—CH$_2$Cl$_2$, 0 to 15% gradient), and produced Thap-OH as white foam (170 mg, 94% yield). MS: m/z (M+1)$^+$: 581.3.

To a solution of Thap-OH (17 mg) in DMSO (1.6 mL) was added folic acid (27 mg, 0.06 mmol), N,N'-dicyclohexylcarbodiimide (DCC, 9.7 mg, 0.077 mmol), and 4-dimethylaminopyridine (DMAP, 3.8 mg, 0.031 mmol), The reaction was stirred at 23° C. for 16 h. The reaction mixture was further diluted with methanol, and was directly purified by HPLC to afford JQ-FT as yellow powder (13 mg, 45% yield). $^1$H NMR (500 MHz, DMSO-d$_6$) δ ppm 0.79-0.89 (m, 5 H) 0.98-1.02 (m, 1 H) 1.11-1.17 (m, 4 H) 1.19-1.33 (m, 19 H) 1.44-1.55 (m, 3 H) 1.64-1.75 (m, 5 H) 1.78-1.82 (m, 8 H) 1.85-1.90 (m, 5 H), 1.95-2.02 (m, 2 H) 2.18-2.35 (m, 6 H) 3.07 (d, J=11.60 Hz, 1 H) 4.26-4.32 (m, 1 H) 4.35 (br. s., 1 H) 4.45-4.52 (m, 3 H) 5.24-5.27 (m, 1 H) 5.39 (t, J=3.51 Hz, 1 H) 5.52 (br.s., 1 H) 5.59 (br.s., 1 H) 6.03-6.19 (m, 5 H) 6.55-6.71 (m, 3 H) 7.61 (d, J=8.85 Hz, 3 H) 8.25 (d, J=7.63 Hz, 1 H) 8.60-8.71 (m, 2 H). MS: m/z (M+1)$^+$: 1004.4.

Scheme 2. Synthesis of fluorescence folic acid derivatives.
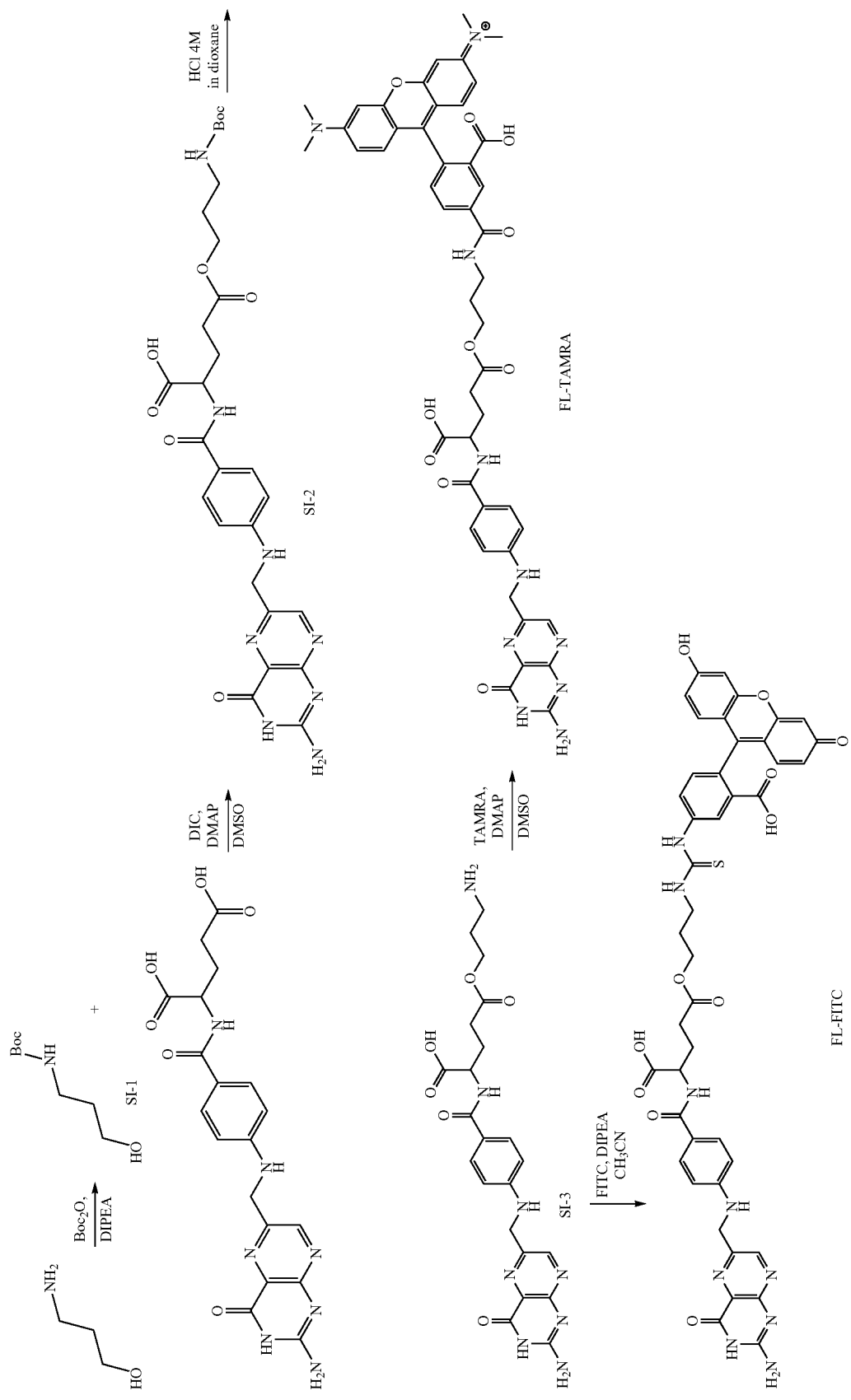

SI-1. (Boc)₂O (2.92 g, 13.36 mmol) was dissolved in THF (20 ml). 3-aminopropanol (1.01 mL, 13.31 mmol) was added and the reaction was stirred at room temperature for 1 h. The reaction was concentrated in vacuo to yield the desired product, ACV-1-076, as a clear oil.

SI-2. Folic acid (502.5 mg, 1.1.4 mmol) and DMAP (692.5 mg, 5.67 mmol) were suspended in DMSO (5 mL). N,N'-Diisopropylcarbodiimmide (DIC, 350.8 uL, 2.27 mmol) was added to the reaction followed by a solution of SI-1 (204.9 mg, 1.17 mmol) in DMSO (2 mL). The reaction was stirred at room temperature and an additional 2 mL of DMSO were added to help solubilize the reactants. The reaction was stirred at room temperature overnight. Water was added to the solution and a yellow-orange solid precipitated out. The reaction was filtered and the filtrate was collected and lyophilized. The residue was re-dissolved in methanol and purified via HPLC to give the desired product, SI-2, as a yellow-orange solid. MS: m/z 599.5 (M+1)⁺.

SI-3. SI-2 was suspended in 4M HCl in dioxane (6 mL) and stirred at room temperature for 3.5 h. The reaction was concentrated in vacuo, redissolved in methanol and purified via HPLC to give the desired product SI-3. MS: m/z 499.4 (M+1)⁺.

FL-FITC. Free amine, SI-3 (37.5 mg, 0.08 mmol) and DIPEA (133.4 uL, 0.77 mmol) were suspended in THF (5 mL). MeCN (1 mL) was added to the reaction to help the solubility of the reaction. FITC (26.7 mg, 0.07 mmol) was then added and the reaction was stirred at room temperature for 3 h. The reaction was purified directly via HPLC to afford the desired product, FT-FITC as a yellow solid. ¹H NMR (500 MHz, DMSO-d₆) d ppm 1.18-1.30 (m, 2 H) 1.56-1.64 (m, 1 H) 1.73-1.82 (m, 2 H) 1.85-2.13 (m, 5 H) 2.31-2.45 (m, 4 H) 3.15-3.21 (m, 6 H) 4.03-4.16 (m, 3 H) 4.32 (s, 1 H) 4.49 (s, 2 H) 6.50-6.72 (m, 17 H) 6.98 (d, J=7.63 Hz, 1 H) 7.09 (d, J=8.24 Hz, 1 H) 7.17 (d, J=8.54 Hz, 1 H) 7.57-7.69 (m, 4 H) 7.70-7.77 (m, 1 H) 8.08-8.25 (m, 3 H) 8.63-8.69 (m, 1 H) 9.07 (s, 1 H) 9.97 (s, 1 H). MS: m/z 887 (M+1)⁺.

FL-TAMRA. Free amine, SI-3 (13.8 mg, 0.028 mmol) and DMA (35.5 mg, 0.289 mmol) were dissolved in DMSO (2 mL). A solution of 5,6-TAMRA succinimidyl ester (10.7 mg, 0.020 mmol) in DMSO (1 mL) was added and the reaction was stirred at room temperature overnight. The reaction was purified via HPLC to afford the desired product, FL-TAMRA as a dark purple solid. ¹H NMR (500 MHz, DMSO-d₆) d ppm 1.13-1.20 (m, 1 H) 1.23 (s, 1 H) 1.77-1.84 (m, 1 H) 1.85-1.93 (m, 2 H) 1.93-2.01 (m, 1 H) 2.04-2.18 (m, 1 H) 2.36 (s, 1 H) 2.42 (t, J=7.32 Hz, 2 H) 3.26 (s, 17 H) 4.10 (t, J=5.95 Hz, 3 H) 4.29-4.42 (m, 1 H) 4.48 (s, 2 H) 5.73-5.77 (m, 1 H) 5.93-5.97 (m, 1 H) 6.52-6.58 (m, 1H) 6.60-6.68 (m, 2 H) 6.95 (s, 2 H) 7.00-7.11 (m, 6 H) 7.54-7.69 (m, 4 H) 7.85-7.96 (m, 1 H) 8.11-8.15 (m, 1 H) 8.17 (d, J=7.93 Hz, 1 H) 8.20-8.25 (m, 1 H) 8.29 (dd, J=7.93, 1.83 Hz, 2 H) 8.62-8.72 (m, 2 H) 8.75-8.82 (m, 1 H) 8.92 (s, 1 H) 9.06 (s, 1 H) 9.97 (s, 1 H). MS: m/z 911.8 (M+1)⁺.

Scheme 3. Synthesis of Thap-Biotin

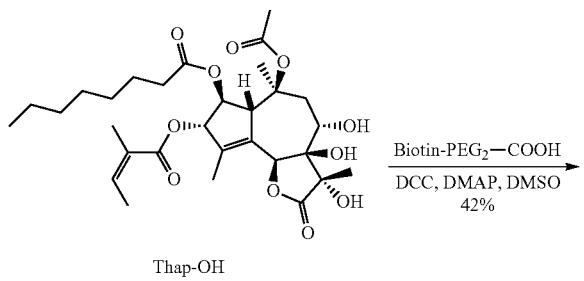

Thap-OH

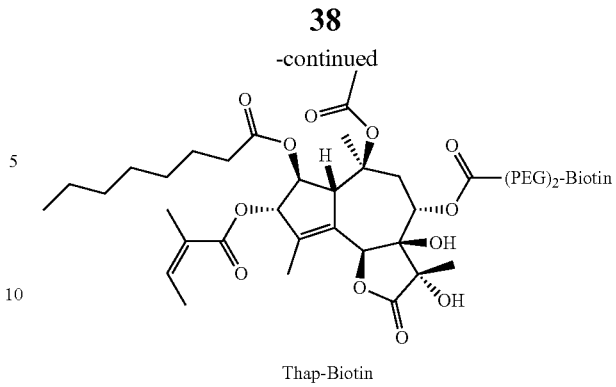

Thap-Biotin

To a solution of Thap-OH (17 mg) in DMSO (1.6 mL) was added Biotin-PEG2-COOH acid (27 mg, 0.06 mmol), DCC (9.7 mg, 0.077 mmol), and DMAP (3.8 mg, 0.031 mmol). The reaction was stirred at 23° C. for 16 h. The reaction mixture was further diluted with methanol, and was directly purified by HPLC to afford Thap-Biotin as colorless oil (13 mg, 42% yield). MS: m/z (M+1)⁺: 1144.6.

Example 2

Expression of Folate Receptor 2 in T-ALL

Figure 7:
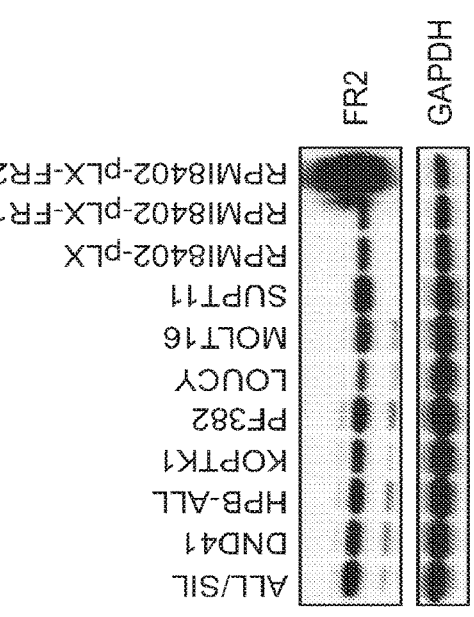
FIG. 7 consists of panels a-3 and pictures folate receptor expression in T-ALL. Panel a tabulates expression of FR1 or FR2 in 17 T-ALL cell lines and in 3 primary human T-ALL samples. Data were collected using quantitative RT-PCR and analyzed using the ΔΔCT method. Panel b shows FR2 level in T-ALL cell lines. Protein expression is detected using an anti-FR2 antibody. Antibody specificity was confirmed including the positive control RPMI 8402-pLX FR2 engineered to stably express high copies of FOLR2. Panel c depicts the structure of FL-TAMRA and FL-FITC. Panel d is a bar graph showing folate up-take in T-ALL cells measured using a TAMRA probe conjugated to folic acid. T-ALL cells have been treated for 6 hours with the indicated concentrations of FL-TAMRA. Error bars denote the mean±SD of 3 replicates. Statistical significance among group for treated vs. vehicle treated (DMSO) (*P≤0.05; P≤0.01; *P≤0.001) was determined by one-way ANOVA using Bonferroni's correction for multiple comparison testing. Statistical analysis were calculated using Prism 5 Software (version 6.05). Panel e is a bar graph showing folate up-take in T-ALL cells and in peripheral blood mononuclear cells (PBMC) pre-treated with 50 ng/mL phorbol 12-myristate 13-acetate (PMA) and 1 μg/ml ionomycin for 6 hours. Treatment with indicated concentrations of FL-FITC or folic acid for 6 hours. Errors bars denote the mean of FITC intensity±SD of 2 replicates. Statistical significance comparing equimolar doses of FL-FITC in PBMC vs. DND41 T-ALL cells (*P≤0.001, **P≤0.0001) was determined by one-way ANOVA using Bonferroni's correction for multiple comparison testing.
Figure 7:
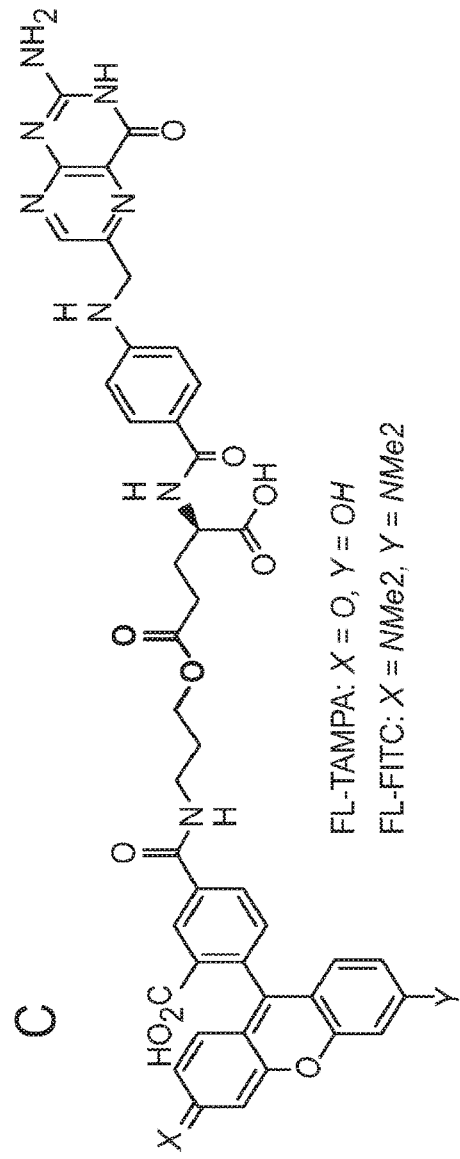

To establish the expression of folate receptor alkies in human T-ALL, we analyzed the mRNA transcript levels of FR1 and FR2 in 17 T-ALL cell lines and in 3 primary leukemia samples by RT-qPCR. We observed that FR2 is abundantly expressed in all leukemia samples while FR1 expression is measurable in only 2/20 cases tested (FIG. 7, panel a). To confirm stable expression of surface polypeptides, we developed methods for FR1 and FR2 flow cytometry. Because FR-isoforms are polypeptides of 220-237 amino acids that share 68-79% sequence identity[7] we first evaluated the specificity of FR antibodies against FR1 and FR2 using a stably transduced NOTCH1-mutated T-ALL cell line (RPMI 8402) overexpressing FR1 or FR2 and established the lack of antibody cross-reactivity by flow cytometry. Western blotting (WB) of lysates from 9 T-ALL cell lines with the isoform-specific FR2 antibody confirmed strong expression of FR2 across all of the samples (FIG. 7, panel b). We did not observe a significant difference in FR2 levels among NOTCH1-mutated (ALL/SIL, DND41, HPB-ALL, KOPT K1, PF382, RPMI 8402) versus WT (Loucy, MOLT16, SUPT11) T-ALL cell lines. These results establish strong expression of FR2, supporting further a rationale for folate-mediated delivery in T-ALL.

To assess functional engagement of the folate receptor on T-ALL cells, we generated fluorescence-ragged folic acid probes. FL-TAMRA and FL-FITC, as tool compounds (FIG. 7, panel c). With FL-TAMRA treatment, all tested T-ALL cell lines showed a concentration-dependent increase in fluorescence signal by flow cytometry, notably independent of NOTCH1 mutational status (FIG. 7, panel d). T-ALL lines demonstrated stronger FL-FITC labeling compared to peripheral blood mononuclear cells (PBMC), providing support for leukemia-specific targeting (FIG. 7, panel e). Taken together, these observations indicate that functional FR2 expression is increased in T-ALL compared to normal cells, further supporting a rationale for folate-mediated delivery in leukemia.

Example 3

Folate-Conjugates Enter T-ALL Cells by FR Binding and Active Transport

Figure 8:
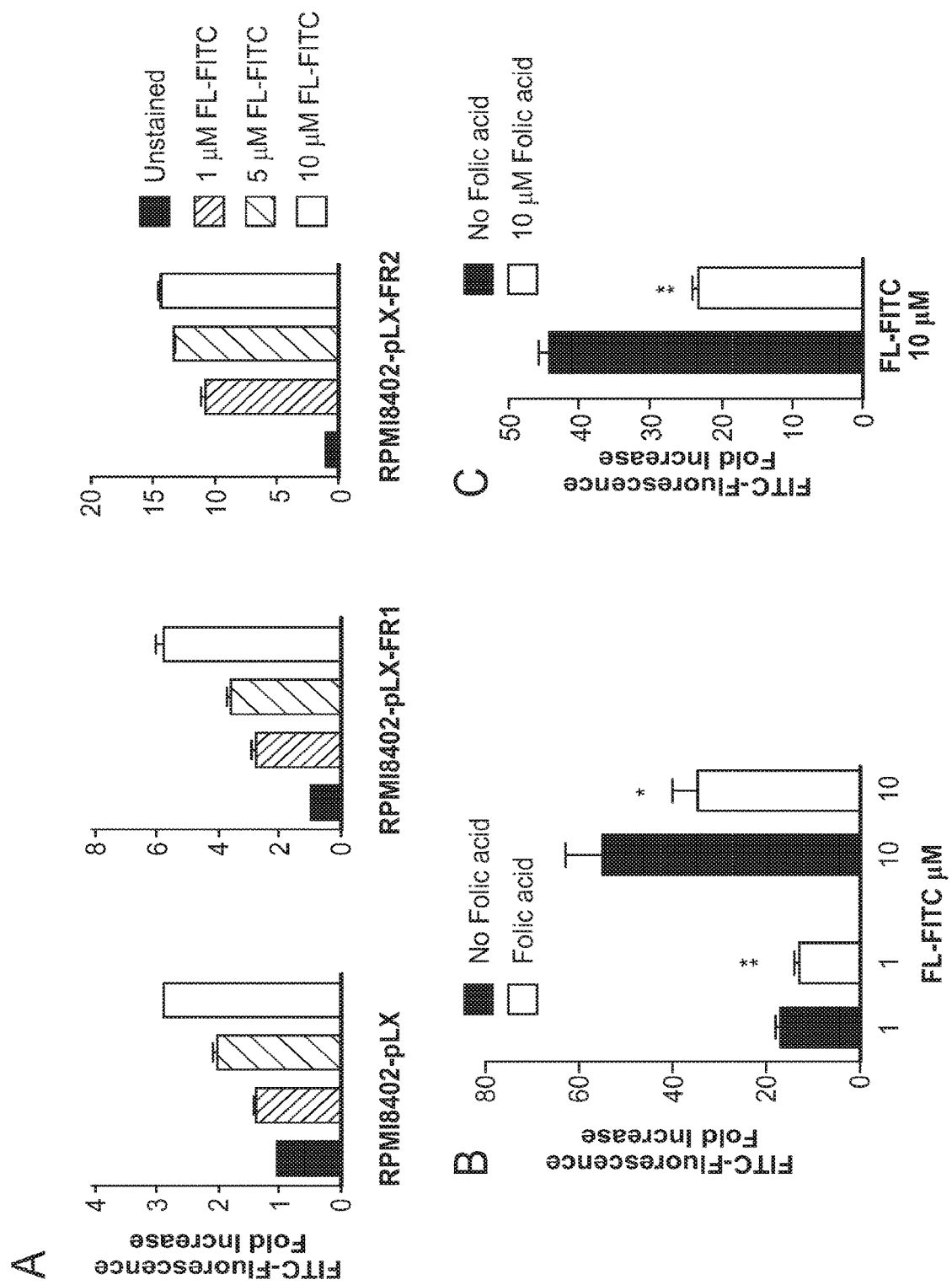
FIG. 8 consists of panels a-f and is a series of images and graphs showing that FL-FITC uptake is Folate-receptor dependent in T-ALL by endocytosis. Panel a is a bar graph depicting FITC fluorescence fold increase upon treatment with indicated concentrations of FL-FITC in T-ALL cells overexpressing FR isoforms. Fluorescence signal is depicted as mean fluorescence intensity relative to untreated control. Errors bars denote the mean±SD of 2 replicates. Panel b is a bar graph depicting FITC fluorescence fold increase upon treatment with indicated concentrations of FL-FITC in T-ALL cells (ALL/SIL) cultured in the presence (red) or absence (black) of folic acid. Fluorescence is expressed as relative activity compared to the untreated control. Errors bars denote the mean of FITC fluorescence intensity±SD of 3 replicates. Statistical significance for all sample pairs in the experiment (*P≤0.05, P≤0.01) was determined by one-way ANOVA using Bonferroni's correction for multiple comparison testing. Panel c is a bar graph depicting FITC fluorescence fold increase in T-All cells (ALL/SIL) cultured in the absence of folic acid 10 µM FL-FITC or 10 µM FL-FITC and 10 µM folic acid. Florescence is expressed as relative activity compared to an untreated control. Error bars denote the mean of fluorescence FITC intensity±SD of 2 biological replicates. Statistical significance among group (P≤0.01) was determined by non-parametric t-test (Mann-Whitney). Panel d contains flow cytometry graphs showing FL-FITC uptake in T-ALL cells in RPMI 8402 cells and RPMI 8402 overexpressing FR isoforms as measured by flow cytometry. Cells were treated with 10 µM FL-FITC and subsequently subjected to an acidic wash with PBS 50 mM Glycine pH 4 (blue) or no wash (red) to eliminate cell surface-bound fluorescence. Untreated cells (dotted line) were used as a control for auto fluorescence. Panel e shows the fluorescence intensity increase in T-ALL cells cultured at 37° C. or 4° C. upon folate-FITC treatment as measured by flow cytometry. Experiments were performed in RPMI 8402 overexpressing FR2 isoforms. Panel d shows FITC fluorescence in four T-ALL cell lines treated with 10 µM FL-FITC and pretreated with vehicle (black) or 10 µM filipin (red). Errors bars denote the mean±SD of 4 cell lines. Statistical significance for difference in treated vs. control samples (*P≤0.05) was determined by non-parametric t-test (Mann-Whitney).

To explore the mechanism of binding and delivery of folate-conjugates in T-ALL, we performed competition and temperature sensitivity studies of the FL-FITC probe. The T-ALL cell Sine RPMI 8402 was engineered to overexpress either FR1 or FR2 and was then treated with increasing concentrations of FL-FITC. We observed a concentration-dependent Increase in the FITC signal with overexpression of either FR1 or FR2 (FIG. 8, panel a). Notably, T-ALL cells overexpressing FR2 demonstrated greater uptake of the folate-conjugate than those overexpressing FR1. We next addressed whether folic acid could compete with the FL-FITC probe for uptake. T-ALL cells were grown in medium depleted of folic acid for 48 hours, treated with FL-FITC (1 or 10 µM), and assessed by flow cytometry. T-ALL cells grown in folate-depleted medium exhibited increased fluorescence compared to control cells incubated in standard folate-replete culture conditions (FIG. 8, panel b), or folate-depleted conditions supplemented with free folate (10 µM; FIG. 8, panel c). Acidic washing of FL-FITC incubated cells did not eliminate fluorescence intensity, supporting internalization of the folate-conjugate fluorescence probe, as opposed to non-specific binding to the cell surface (FIG. 8, panel d).

FL-FITC uptake also showed an energy-dependency. T-ALL cells with FR2 overexpression cultured at 4° C. were unable to take up the FL-FITC. This observation supports an active, endocytic mechanism of uptake, as low temperature blocks endocytosis at 4° C. due to altered membrane fluidity (FIG. 8, panel e), in keeping with prior reported folate-conjugate studies. In order to determine if the endocytic process is caveolae-mediated, we tested FT-FITC uptake in T-ALL cells that were pretreated with filipin, a transient inhibitor of caveolin-mediated endocytosis. The filipin pretreated T-ALL cells produced significantly reduced FITC fluorescence signal (mean percentage reduction 38.9±2.5) confirming that the folate conjugate uptake into the cell is mediated by caveolar transport (FIG. 8, panel f). Together, these results demonstrate that folate-conjugated probes are internalized into T-ALL cells by FR-dependent, caveolae-mediated endocytosis.

Example 4

Thap-OH Inhibits NOTCH1 Signaling in T-ALL

To test the hypothesis that Thap-OH targets SERCA in T-ALL cells, we first performed a competitive pull-down assay in which protein lysates were treated with a novel biotinylated derivative of thapsigargin (Thap-Biotin), alone or in the presence of increasing concentrations of free, competitive Thap-OH. Binding to Thap-Biotin in a complex mixture was confirmed by immunoblot, as free Thap-OH competed off biotinylated thapsigargin from SERCA2 and SERCA3 (FIG. 9, panel a).

We previously described that the SERCA inhibitors thapsigargin and cyclopiazonic acid impair NOTCH1 maturation leading to an accumulation of full-length, unprocessed polypeptides in the endoplasmic reticulum/Golgi subcellular compartment. An immediate consequence of SERCA inhibition is a decrement in NOTCH1 protein display on the surface of T-ALL cells. The treatment of T-ALL cells with Thap-OH resulted in a concentration-dependent reduction in NOTCH1 expression on the cell surface by flow cytometry, as was observed with control thapsigargin treatment. Thap-OH was again found to be less potent than the natural product, as predicted from prior studies (FIG. 9, panel b). To further support the hypothesis that Thap-OH impairs mutant NOTCH1 maturation, we evaluated levels of full-length, transmembrane and activated NOTCH1 (ICN1) by WB. Lysates from T-ALL cell lines treated with 1 µM Thap-OH were immunoblotted with an antibody specific for the cytoplasmic portion of NOTCH1 that recognizes both unprocessed NOTCH1 (FL-N1) (~270 kDa) and the furin-processed transmembrane subunit (TM-N1) (~110 kDa). Consistent with the flow cytometry data, Thap-OH reduced the levels of the furin-processed transmembrane NOTCH1 subunit, but not the unprocessed full-length NOTCH1 precursor, in multiple T-ALL cell lines (FIG. 9, panel c). Moreover, Thap-OH decreased ICN1 levels in T-ALL cells, suggesting that the cleavage product retains the potent anti-NOTCH1 properties observed with SERCA inhibition.

Figure 9:
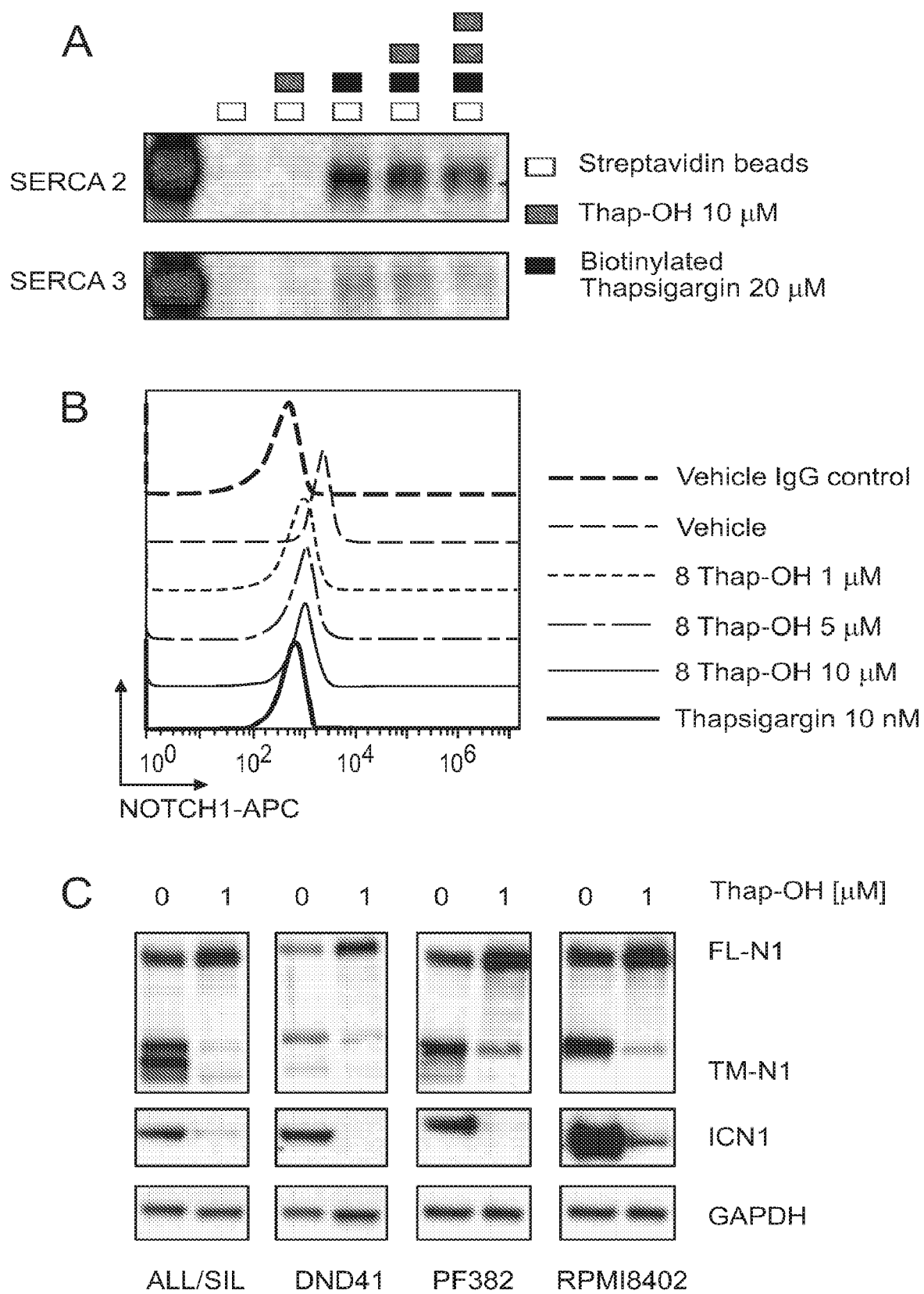
FIG. 9 consists of panels a-g and depicts that Thap-OH demonstrates anti-NOTCH1 and anti-leukemia properties in T-ALL in vitro. Panel a shows the effect of Thap-OH on SERCA binding. Lysates from T-ALL cells (ALL/SIL) were co-treated with the indicated concentrations of biotinylated thapsigargin or Thap-OH for 6 hours and subjected to streptavidin pulldown for 24 hours. The immunoblot was stained with SERCA2 and SERCA3 antibodies. Panel b shows the effect of 24 hours of Thap-OH treatment on NOTCH1 cell surface staining as assessed by flow cytometry. Panel c shows the effect of Thap-OH treatment for 24 hours on NOTCH1 (N1) processing and activation in T-ALL cell lines all with HD mutations (DND41 and ALL/SIL (L1594PΔPEST), PF382 (L1575PΔPEST) and RPM1 8402 (ins1584PVELMPPE). The blot was stained with an anti-body against the C-terminus of NOTCH1 that recognizes both the furin-processed NOTCH1 transmembrane subunit (TM) and the unprocessed NOTCH1 precursor (FL). The immunoblot was also stained with anti-ICN1 antibody (Val1744) and GAPDH as a loading control. Panel d shows the effect of Thap-OH treatment on cell viability after 72 hours of treatment in NOTCH1 mutated T-ALL cells (ALL/SIL, DND41, PF382, RPMI 8402) or WT (Loucy, MOLT16, SUPT11). Statistical significance for mutated vs WT (*P≤: 0.05, **P≤0.01) was determined by one-way ANOVA with Bonferroni's correction for multiple comparison testing. Panel e shows the effect of Thap-OH treatment (24 hours) on processing of NOTCH1 mutant (ALL/SIL) or WT (Loucy, MOLT16) NOTCH1. NOTCH1 (N1) was detected with an antibody against the C-terminus of NOTCH1 that recognizes the form-processed NOTCH1 transmembrane subunit (TM) and the unprocessed NOTCH1 precursor (FL). GAPDH was used as loading control. Panel f shows the effect of Thap-OH treatment (6 and 12 hours) on NOTCH1 cell surface staining as assessed by flow cytometry. Panel g shows the effect of Thap-OH treatment (24 hours) on FR2 in T-ALL cells. Immunoblot was stained with an antibody against FR2. Vinculin was used as a loading control.

As expected, treatment with Thap-OH was associated with a decrease in T-ALL cell viability, as measured by dose-ranging ATP content assays (FIG. 9, panel d). Furthermore, the selectivity for mutant compared to wild-type NOTCH1 was retained with Thap-OH; mutant T-ALL cells were more sensitive to the effects of Thap-OH than NOTCH1 WT cells (FIG. 9, panel d), and there was no effect on NOTCH1 maturation in the WT cell lines at the concentrations tested (FIG. 9, panels e and f). Thus, cell lines carrying NOTCH1 alleles with HD domain, mutations were more sensitive to Thap-OH than cells with WT NOTCH1 alleles.

Thapsigargin is a known inducer of the unfolded protein response (UPR). As such, its derivatives may trigger a cellular response that affects the stable expression or trafficking of folate receptors. To exclude that FR2 is a target of UPR, we treated T-ALL cell lines with increasing concentrations of Thap-OH for 24 hours. No change in FR2 expression was observed in WB (FIG. 9, panel g), indicating that FR2 is not affected by Thap-OH at concentrations targeting NOTCH1.

Together these data demonstrate that Thap-OH preferentially inhibits mutant NOTCH1 receptors while sparing WT NOTCH1 and FR2 expression, supporting Thap-OH as a suitable and targeted payload for folate-conjugation.

Example 5

Mechanism of Drug Delivery for Thapsigargin-Folic Acid Conjugates

Figure 2:
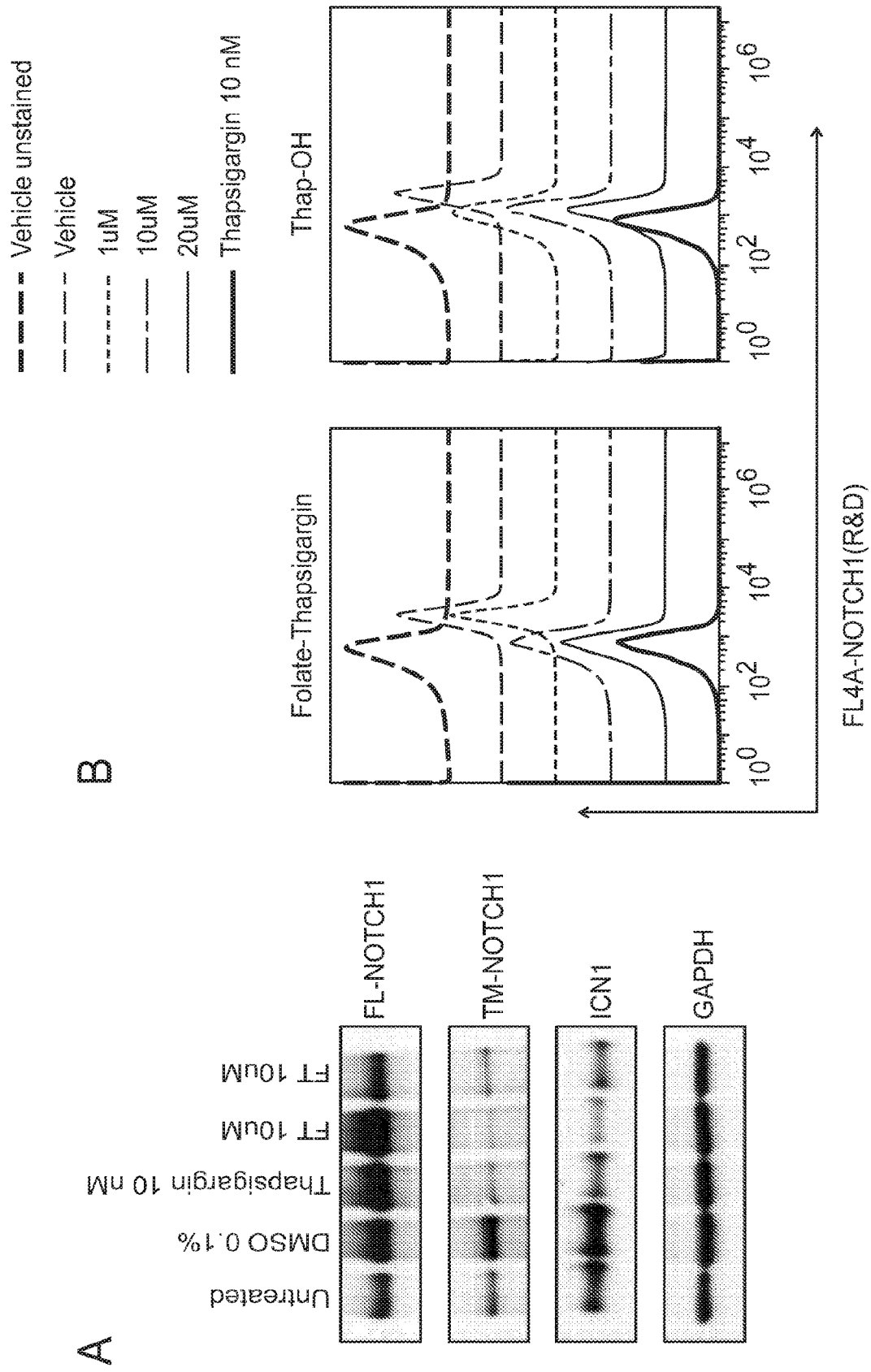
FIG. 2 consists of panels A-C and contains a series of images demonstrating that thapsigargin-folic acid conjugate Folate-Thap (FT) recapitulates the elicit of thapsigargin at higher concentration.
Figure 3:
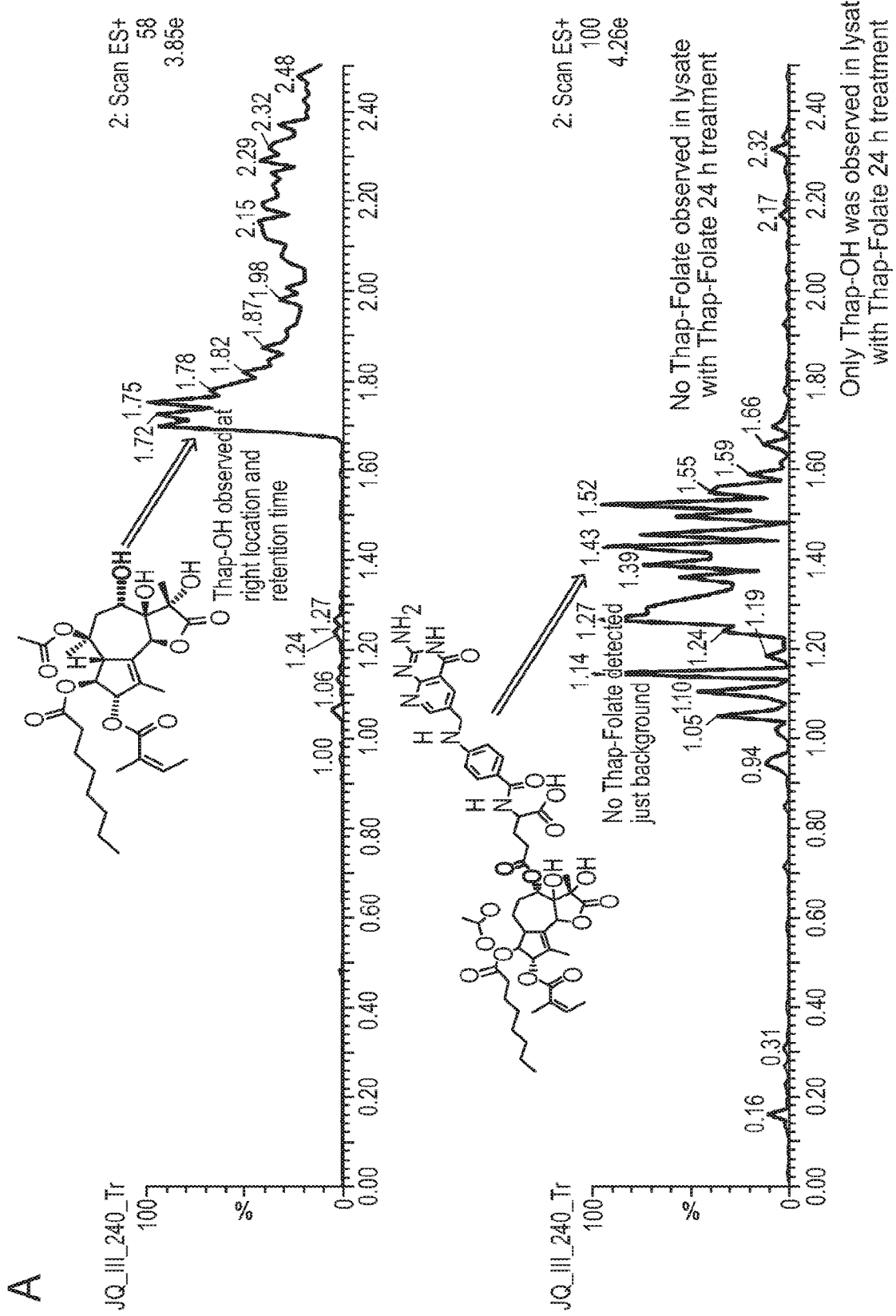
FIG. 3 consists of panels A-D and shows results of experiments that determined small molecule delivery by folate.

Both Folate-Thap (JQ-FT) and Thap-OH were tested in T-ALL cell lines with 24 h treatment. Similarly to thapsigargin, JQ-FT caused loss of ICN1, loss of trans-membrane NOTCH, and accumulation of full length NOTCH. Lysates were prepared after treatment with indicated doses of thapsigargin, JQ-FT or Thap-OH for 24 hr. The blot shown was stained with an antibody against the C-terminus of NOTCH1 that recognizes both the furin-processed NOTCH1 transmembrane subunit (TM) and the unprocessed NOTCH1 precursor (FL) (FIG. 2A). GAPDH was used as a loading control. Western blots were stained with antibodies specific for γ-secretase-cleaved NOTCH 1 (Val144, Cell Signaling, Beverly, Mass., USA), or the C-terminus of NOTCH1 (SC-6014 (C-20) Santa Cruz Biotechnology, Santa Cruz, Calif., USA). Control stains were carried out with antibodies specific for GAPDH (137179, Santa Cruz Biotechnology).

Blots were developed with anti-rabbit-HRP (NA9340V, Amersham, Pittsburgh, Pa., USA) or anti-mouse-HRP (NA9340V or NA9310V, Amersham). Staining was quantified using ImageQuant TI V 7.0 (GE Health Care, Piscataway, N.J., USA).

The Thap-OH, on the other hand, showed much lower activity. As a further test of the idea that JQ-FT acts by preventing NOTCH1 activation in a manner similar to thapsigargin, the NOTCH1-dependent T-ALL cell lines RPMI-8402 were transduced with empty MigRI vector or with ICN1, which lies downstream of the γ-secretase cleavage step in Notch activation. Viral supernatant production and retroviral infections were performed as described for MigRI retroviral vectors (Aster, J. C., et al. "Essential roles for ankyrin repeat and transactivation domains in induction of T-cell leukemia by NOTCH1." Mol. Cell. Biol. 2000; 20:7505-7515). Transduction efficiency for MigRI was monitored by assessing GFP expression with a FACScan flow cytometer (BD, Franklin Lakes, N.J., USA) (Aster et al., Mol. Cell. Biol. 2000; 20:7505-7515). After viral infection, GFP-positive cells were sorted by flow cytometry with a FACSAria II (BD, Franklin Lakes, N.J., USA). The loss of viability caused by JQ-FT was on target for NOTCH1 since overexpressing an exogenous ICN1 partially rescues the observed phenotype. Therefore, JQ-FT can recapitulate the Thapsigargin effect with the delivery mechanism of folate.

The NOTCH loss was measured via flow cytometry. Cell surface NOTCH1 was evaluated by staining non-permeabilized cells with monoclonal anti-human NOTCH1 antibody (R&D FAB5317P, Minneapolis, Minn., USA), Both JQ-FT and Thap-OH show NOTCH loss, but the JQ-FT was more similar to thapsigargin at 20 uM. Thap-OH had a reduced effect (Skytte D M et al, Bioorganic Med. Chemistry, 2010, 5634) compared to Thapsigargin itself. The recapitulation of the thapsigargin effect by JQ-FT is hypothesized to be due to the delivery strategy introduced by folate. The treatment of T-ALL cell lines with Folate-Thap (FIG. 2, panel C) produced an antiproliferation effect. Here cell growth was assessed using the Promega Cell-Titer Glo ATP-based assay (Promega, Madison, Wis., USA). Luminescence was measured using a Fluostar Omega instrument (BMG-labtech, Ortenberg, Germany).

Figure 6:
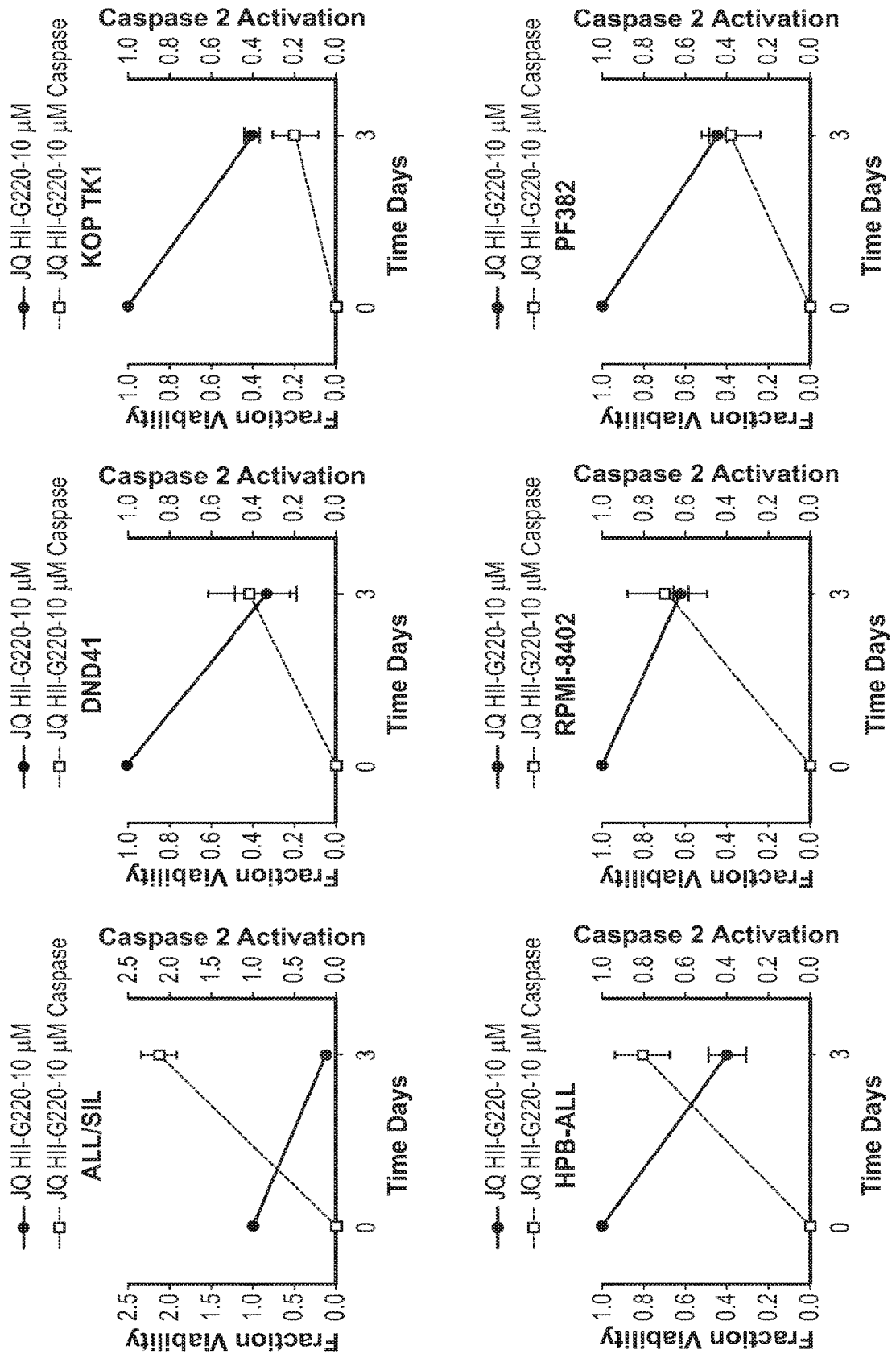
FIG. 6 contains a series of graphs measuring apoptosis in a panel of cell lines.

Treatment of a panel of cell lines with Folate-Thap produced an apoptotic effect, as measured by Caspase 2 (FIG. 6). Cells were grown in 384-well plates and treated for 72 hours with the indicated dose of Folate-Thap. Apoptosis was measured using a luminescence assay developed by Promega.

Figure 10:
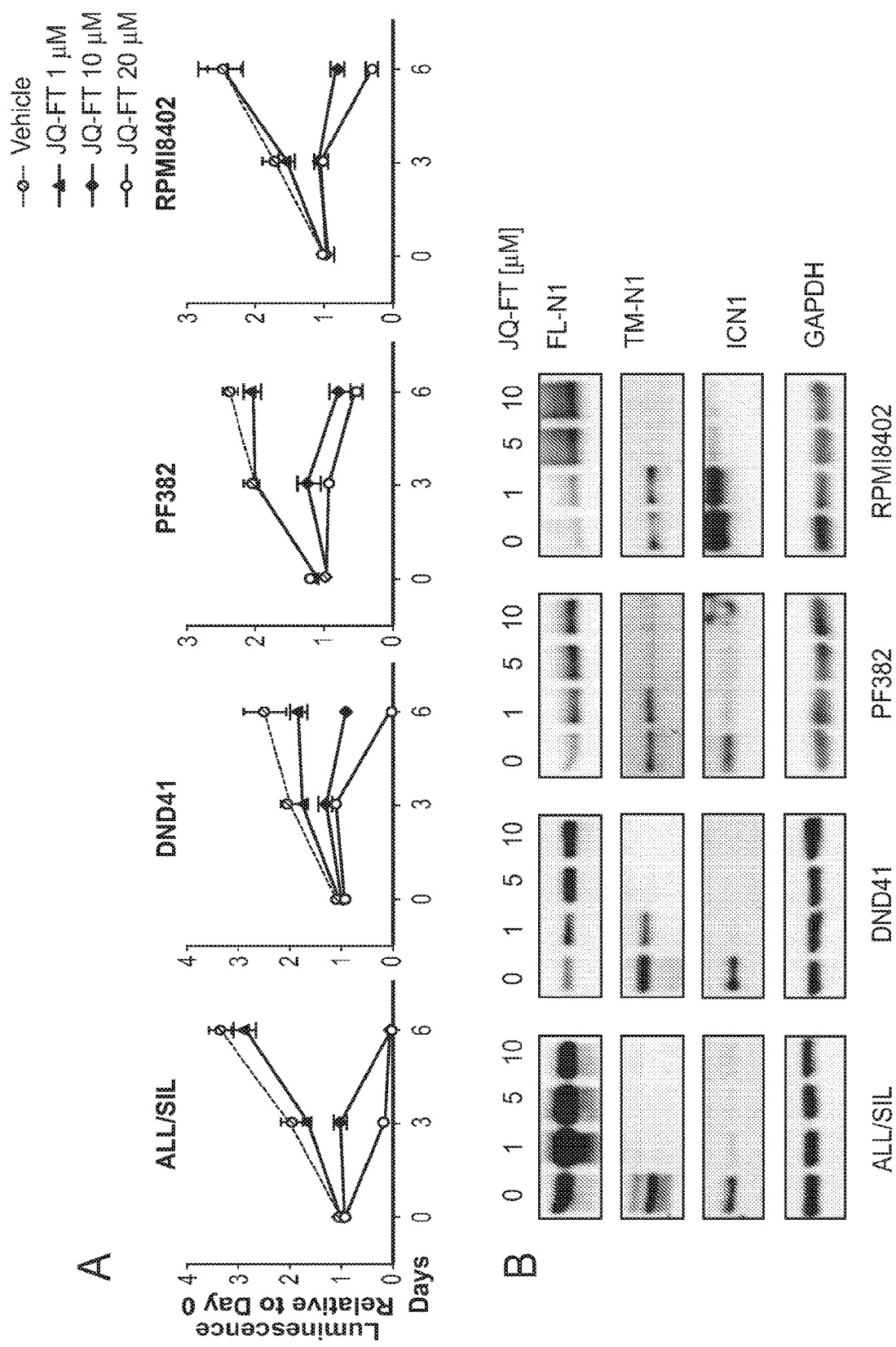
FIG. 10 consists of panels a-f and shows that JQ-FT demonstrates anti-leukemia properties in T-ALL in vitro. Panel a shows the effect of JQ-FT treatment on cell growth. Errors bars denote mean±SD of 4 replicates. Panel b shows the effect of JQ-FT treatment (24 hours) on NOTCH1 (N1) processing and activation in T-ALL cell lines all with HD mutations. The blot was stained with an antibody against the C-terminus of NOTCH1 that recognizes both the furin-processed NOTCH1 transmembrane subunit (TM) and the unprocessed NOTCH1 precursor (FL). The immunoblot was also stained with anti-ICN1 antibody. GAPDH was used as a loading control. Panel c shows the mean expression of NOTCH1 target genes in T-ALL cells (ALL/SIL, DND41) treated for 24 hours with the indicated concentrations of thapsigargin, JQ-FT, Thap-OH, folic acid or the GSI compound E was determined by qRT-PCR. Error bars indicate the mean±SD of 4 replicates. Data were analyzed using the ΔΔCT method and plotted as a percentage relative to the control gene RPL13A. Statistical significance among groups for treated vs. vehicle (DMSO) samples (*P≤0.0001) was determined by one-way ANOVA with Bonferroni's correction for multiple comparison testing. Panel d shows the effect of JQ-FT treatment (24 hours) on NOTCH1 processing so PDX cells in vitro. The blot was stained with an antibody against the C-terminus of NOTCH1 (N1) that recognizes both the furin-processed NOTCH1 transmembrane subunit (TM). GAPDH was used as a loading control. Panel e shows immunofluorescence analysis of JQ-FT treatment (24 hours) on NOTCH1 activation in permeabilized PDX cells in vitro. Cells were probed with an anti-NOTCH1 antibody (green) and nuclei were counterstained with DAPI. Panel f shows expression of indicated NOTCH1 target genes in T-ALL PDX cells treated with JQ-FT for 24 hours was determined by qRT-PCR. Error bars indicate the mean±SD of 4 replicates. Data were analyzed using the ΔΔCT method and plotted as a percentage relative to the control gene RPL13A. Statistical significance (*P≤0.001. ****P≤0.0001) for treated vs. vehicle (DMSO) was determined by one-way ANOVA with Bonferroni's correction for multiple comparison testing.

The effects of JQ-FT in a panel of T-ALL cell lines that contain activating mutations in the HD domain of NOTCH1 and/or protein stabilizing deletions within the PEST degradation domain. In all T-ALL cell lines studied, JQ-FT impaired cell growth, leading to a G1 cell cycle arrest and rapid induction of apoptosis (10 μM; FIG. 10, panel a). As expected based on our FL-FITC uptake studies, a greater effect on cell viability was observed in cell lines overexpressing FR1 or FR2.

As observed with thapsigargin and Thap-OH, treatment of T-ALL cell lines with JQ-FT led to accumulation of full length NOTCH1 (FIG. 10, panel b). A decrement of transmembrane NOTCH1 (TM-N1) was confirmed by WB and flow cytometry analysis (FIG. 10, panel b). Loss of ICN1 (FIG. 10, panel b) caused the suppression of NOTCH1 target genes as measured by RT-PCR (FIG. 10, panel c). In order to establish if the effects of JQ-FT on cell viability were due to impaired NOTCH1 activation, the NOTCH1-dependent T-ALL cell line RPMI 8402 was transduced with MigR1-ICN1 to rescue effects on full-length NOTCH1 processing, versus an empty MigR1 vector control. Exogenous expression of ICN1 attenuated the growth inhibitory effects of JQ-FT, in keeping with the function of ICN1 downstream of ER processing and surface γ-secretase cleavage in Notch pathway activation.

To assess the translational significance of these findings, we studied patient-derived xenografts (PDX) from T-ALL patients at the Dana-Farber Cancer Institute. JQ-FT treatment of NOTCH1-mutated PDX cells in vitro resulted in loss of transmembrane NOTCH1, leading to the depletion of detectable ICN1 (FIG. 10, panels d, e). In contrast, no effect was observed in PDX T-ALL cells possessing WT NOTCH1 (FIG. 10, panel d). Consistent with these results, no transcriptional changes were observed in NOTCH1 target genes in WT PDX samples while expression of canonical NOTCH1 target genes, DTX and MYC, were decreased in the NOTCH1 mutant samples (FIG. 10, panel f). These results provide strong support for the mechanistic thesis that mutated NOTCH1 receptors are more sensitive to JQ-FT treatment in human T-ALL, prompting proof-of-concept studies in T-ALL models in vivo.

Example 6

Fluorescence Analysis of Folate-Thap Delivery

In order to validate the delivery of the Thap-OH, LCMS analysis of the cell lysate and the media was used to detect the presence of both Folate-Thap (FT) and Thap-OH. FT was not detected in either cell culture media (24 h treatment) or cell lysate. Thap-OH was detected in cell lysate, however, only after cells were treated with FT. This data supported that FT was taken into the cell at the folate receptor (FR) and then the folate receptor is cleaved within the cell, yielding Thap-OH. To directly visualize the folate delivery of a small molecule, folic acid derivatives with appended fluorophores were designed. Both Folate-FITC, suitable for flow cytometry studies, and Folate-TMARA, suitable for high-throughput fluorescence plate readers, were evaluated in vitro to determine the delivery mechanism. The update of Folate-FITC was observed in T-ALL treatment of Folate-FITC with flow cytometry. Further, when free folic acid was added to T-ALL culture, the folic acid competed away the folate derivatives. This data further confirms that the folate derivatives bind to the FR in the same manner as free folic acid.

Figure 5:
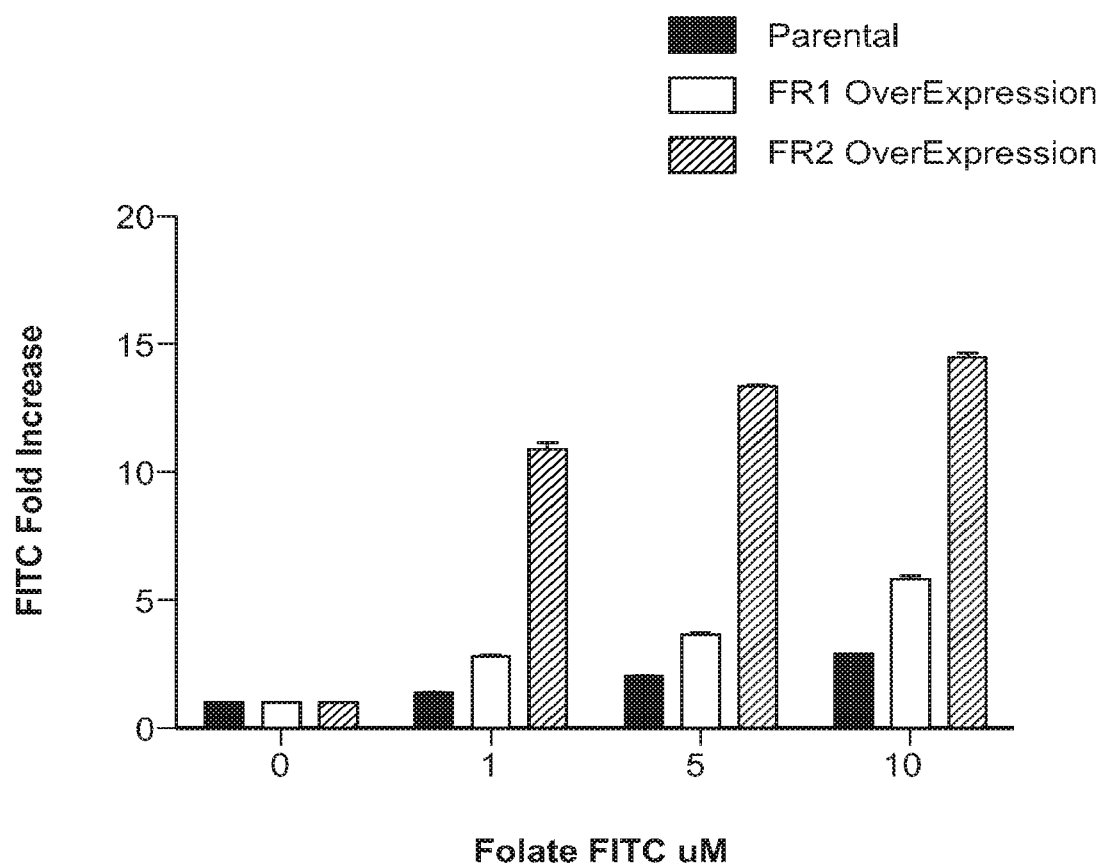
FIG. 5 is a bar graph demonstrating that uptake of the folate-conjugated molecule is dependent on expression of the folate receptor.

Folate-FITC was further used to demonstrate that the uptake of folate-conjugated molecules is dependent on the expression of the folate receptor (FIG. 5). T-ALL cell lines were transduced with virus containing particles expressing a PLX empty vector or PJLX-FOLR1 or PLX-FOLR2. Transduction efficiency was confirmed by RT-qPCR measuring FOLR1 or 2 transcripts. Cells were subsequently treated with the indicated doses of Folate-FITC, and fluorescence intensity was quantified by flow-cytometry. Results were expressed as fold increase relative to untreated controls.

Example 7

JQ-FT Attenuates NOTCH1-Driven T-ALL In Vivo

Figure 11:
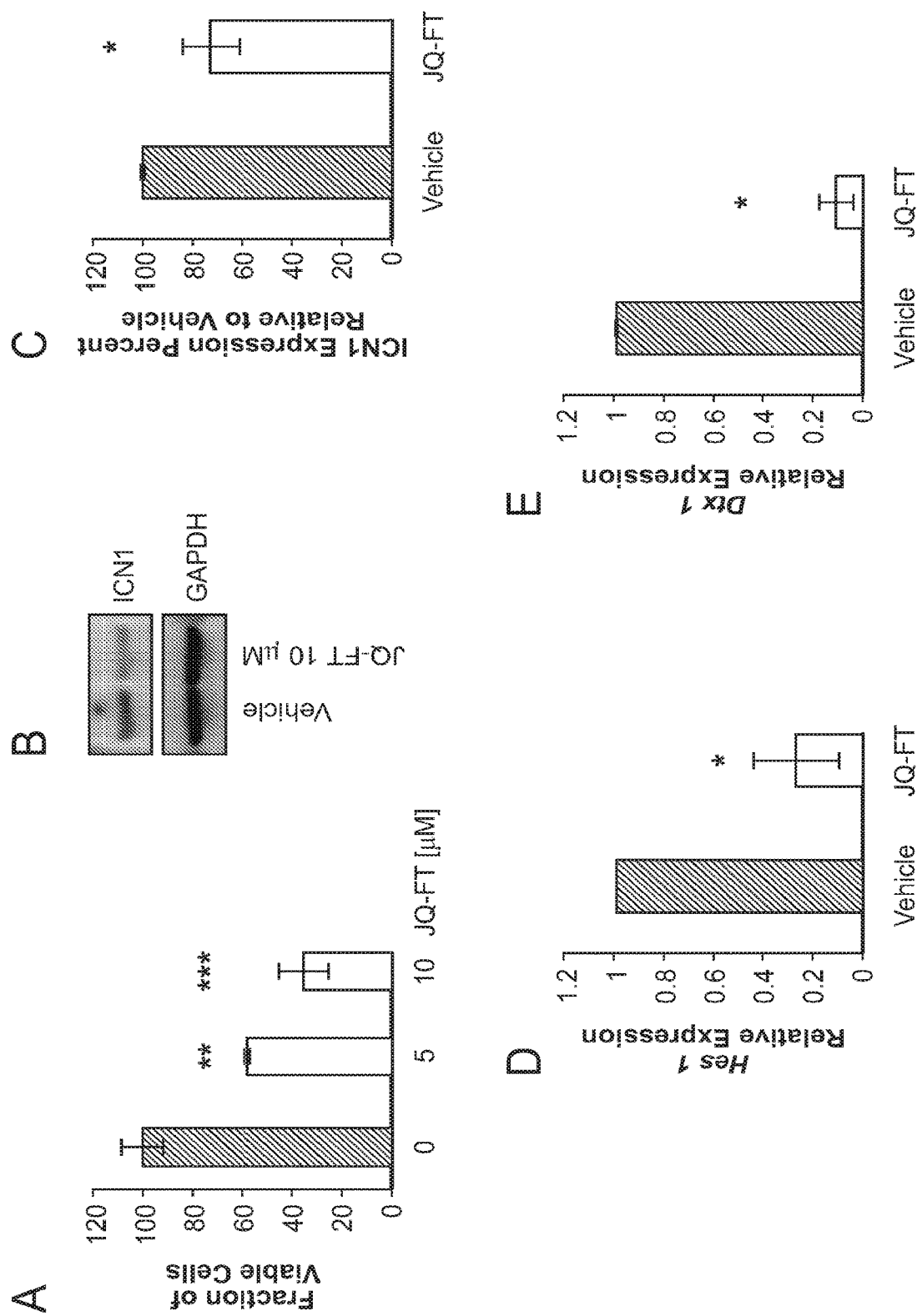
FIG. 11 consists of panels a-I and shows that JQ-FT demonstrates activity in T-ALL mouse model. Panel a shows the effect of JQ-FT treatment on cell growth (72 hours) in murine NOTCH1 L1601P ΔPEST expressing leukemia lymphoblasts. Viability data is represented as percentage relative to vehicle treatment and errors bars denote mean±SD of 3 replicates. Statistical significance of treated vs. vehicle (DMSO) samples (*P≤0.01; *P≤0.001) was determined by one-way ANOVA with Bonferroni's correction for multiple comparison testing. Panel b shows the effect of JQ-FT on ICN1 levels in murine NOTCH1 L1601P ΔPEST expressing leukemia lymphoblast cells. The immunoblot contains cell lysates stained with anti-ICN1 antibody (Val1744) after treatment with the 10 µM of JQ-FT for 24 hours in vitro. GAPDH was used as a loading control ICN1 loss was quantified and bar graph (panel e) corresponds to the results of the quantification of three independent experiments. Statistical significance of treated vs. vehicle (DMSO) samples (*P≤0.05) was determined by Student's t-test. Expression of indicated NOTCH1 target genes Hes1 (panel d) and Dtx1 (panel e) in murine NOTCH1 L1601P ΔPEST expressing leukemia lymphoblasts treated with 10 μM JQ-FT for 24 hours was determined by qRT-PCR. Error bars indicate the mean±SD of 3 replicates. Data were analyzed using the ΔΔCT method and plotted as a percentage relative to the control gene Gapdh. Statistical significance for treated vs. vehicle (DMSO) (*P≤0.05) was determined by Student's t-test. Panel f shows a histological analysis of the spleen and the liver in a NOTCH1 L1601P ΔPEST murine model treated with JQ-FT 60 mg/Kg or vehicle for five days. The spleen and the liver of all mice were examined; representative results for one control animal and one JQ-FT-treated animal are shown. Formalin-fixed, paraffin-embedded tissue sections were stained using the hematoxylin and eosin stain (H & E) method. Growth suppression of lymphoblasts (dark purple) was observed in JQ-FT treated animals. Panel g shows the effect of JQ-FT on T-ALL growth in a NOTCH1 L1601P ΔPEST murine model. Anti-leukemic activity of JQ-FT was assessed by measuring spleen weight upon 5 days of JQ-FT treatment (60 mg/kg I.P) or vehicle (65% D5W+30% PEG-400+5% Tween-80only). The chart shows fold change tumor burden for each animal (each dot) and the horizontal bar represents the mean of the four animals per group. Statistical significance for treated vs. vehicle (*P≤0.05) was determined by non-parametric t-test (Mann-Whitney). Panel h shows the antileukemic activity of JQ-FT on bone marrow NOTCH1 L1601P ΔPEST GFP positive leukemia ceils upon 5 days of JQ-FT treatment (60 mg/kg I.P) or vehicle (65% D5W+30% PEG-400+5% Tween-80only). Error bars indicate mean±SD of 4 replicates (of the 4 animals of each group). Statistical significance for treated vs. vehicle (*P≤0.05) was determined by non-parametric t-test (Mann-Whitney). Panel I shows the effect of JQ-FT on Notch activation in a NOTCH1 L1601P ΔPEST murine model. The immunoblot contains splenic cell lysates stained with anti-ICN1 antibody (Val1744) after treatment with the 60 mg/Kg of JQ-FT for 5 days. GAPDH was used as a loading control. ICN1 loss was quantified and bar graph (j) corresponds to the results of the quantification. Statistical significance for treated vs. vehicle (*P≤0.05) was determined by Student's t-test.

In vitro studies provide valuable mechanistic insights but may not recapitulate tumor micro-environment and metabolic conditions in vivo. Indeed, a significant limitation of research on folate-conjugate drugs is the inconsistency between free folate concentrations (and other middle metabolites) in culture conditions in vitro versus in vivo. High levels of free folic acid in the sera may block the binding and uptake of JQ-FT in FR2-positive T-ALL compromising the anti-NOTCH1 leukemia effect observed in vitro. To explore the therapeutic efficacy of JQ-FT in vivo, we studied effects on a syngeneic T-ALL mouse model carrying a NOTCH1 L1601P ΔPEST, a common mutation observed in the human disease. First, leukemia cells obtained from this model were treated with JQ-FT for 24 hours in vitro. Consistent with the results observed in cell lines and in PDX cells, ex vivo treatment with JQ-FT diminished the proliferation (FIG. 11, panel a), ICN1 expression (FIG. 11, panels b and c) and transcription of canonical NOTCH1 targets Hes1, and Dtx1 (FIG. 11, panels d and e).

Though the JQ-FT conjugate has not, as yet, been optimized for pharmacologic properties, we are eager to explore the utility of the compound as an in vivo chemical probe, while assessing putative tolerability of folate-conjugated thapsigargins. We first established the maximal tolerated dose (MTD) of JQ-FT as 60 mg/kg/day in mice, as administered by daily intraperitoneal injection. Notably, this tolerated concentration is 150-fold improved over our prior established MTD of unconjugated thapsigargin. We therefore initiated treatment studies of JQ-FT (60 mg/kg IP daily) in mice with established T-ALL. Following five days of treatment, an evident decrease in tumor growth was observed, confirmed pathologically by a decrease of leukemic infiltration in spleen and liver (FIG. 11, panel f) and clinically by a reduction in spleen weight (FIG. 11, panel g). Bone marrow infiltration by T-ALL, the primary site of human disease, was markedly inhibited by JQ-FT, as confirmed by flow cytometric analysis immunohistochemistry for GFP+ leukemia cells (FIG. 11, panel h). Pharmacodynamic modulation of the Notch pathway was importantly validated by measurement of reduced ICN1 expression in T-ALL cells from JQ-FT treated animals, as compared to vehicle-treated controls (FIG. 11, panels i and j).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound having the structure of formula (II):

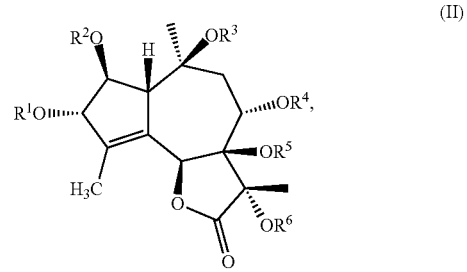

or a pharmaceutically acceptable salt thereof;

wherein $R^1$, $R^2$, $R^3$, $R^4$, $R^5$, and $R^6$, independently for each occurrence, comprises a cell-targeting ligand moiety, or is H, (CO)hydrocarbyl, COOH, hydrocarbyl, (CO)(NH)hydrocarbyl, or (CO)O-hydrocarbyl; and wherein at least one of $R^1$, $R^2$, $R^3$, $R^4$, $R^5$, and $R^6$ comprises a cell-targeting ligand moiety; and the cell-targeting ligand moiety comprises a residue of folic acid.

2. The compound of claim 1, wherein the cell-targeting ligand moiety binds to a receptor expressed on the surface of a cell.

3. The compound of claim 2, wherein the receptor expressed on the surface of the cell is a folic acid receptor.

4. The compound of claim 1, wherein the at least one of $R^1$, $R^2$, $R^3$, $R^4$, $R^5$, and $R^6$ that comprises a cell-targeting ligand moiety further comprises a linking moiety.

5. The compound of claim 4, wherein the linking moiety comprises one or more bonds that are cleavable under physiologic conditions.

6. The compound of claim 5, wherein the linking moiety comprises at least one moiety selected from amide, carbonate, carbamate, ether, ester, disulfide, sulfonate ester, sulfonamide, acetal, and ketal.

7. The compound of claim 1, wherein the cell-targeting ligand moiety is cleaved from the pharmacophore after the compound is delivered to a cell.

8. The compound of claim 1, wherein $R^1$, $R^2$, $R^3$, $R^4$, $R^5$, and $R^6$, independently for each occurrence, comprises a cell-targeting ligand moiety, or is H or (CO)hydrocarbyl.

9. The compound of claim 1, wherein $R^4$ comprises a residue of folic acid.

10. The compound of claim 1, having the structure of formula (III),

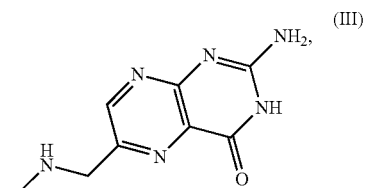
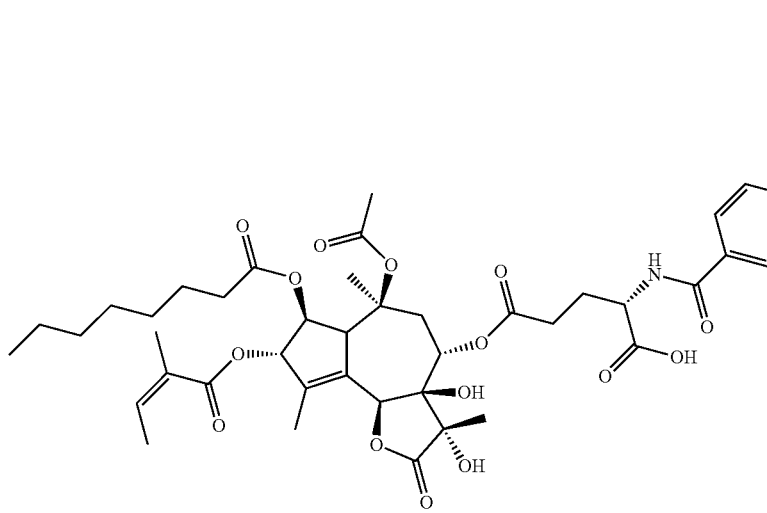

or a pharmaceutically acceptable salt thereof.

11. A pharmaceutical composition, comprising a compound of claim 1, and a pharmaceutically acceptable excipient.

12. A method of treating cancer, comprising administering to a patient in need thereof a therapeutically effective amount of a compound of claim 1.

13. The method of claim 12, wherein the cancer comprises cancer cells over-expressing a folic acid receptor.

14. The method of claim 12, wherein the cancer is characterized by aberrant activity of the NOTCH1 gene.

15. The method of claim 12, wherein the cancer is ovarian cancer, non-small cell lung cancer, breast cancer, multiple myeloma, chronic lymphocytic leukemia (CLL), acute lymphoblastic leukemia (ALL), B-cell lymphoma, medulloblastoma, colorectal cancer, or melanoma.

16. The method of claim 12, further comprising administration of an additional chemotherapeutic agent.

17. A method of inhibiting activation of NOTCH1, comprising contacting NOTCH1 with an amount of a compound of claim 1 effective to inhibit NOTCH1.

* * * * *